(12) United States Patent
Biggadike et al.

(10) Patent No.: US 6,777,400 B2
(45) Date of Patent: *Aug. 17, 2004

(54) ANTI-INFLAMMATORY ANDROSTANE DERIVATIVE COMPOSITIONS

(75) Inventors: Keith Biggadike, Stevenage (GB); Steven John Coote, Stevenage (GB); Andrew Craig, Tonbridge (GB); Victor Jacewicz, Tonbridge (GB); Michael J. Millan, Tonbridge (GB); John F. Seager, Stevenage (GB); Andrew L. Theophilus, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 22 days.

This patent is subject to a terminal disclaimer.

(21) Appl. No.: 10/241,658

(22) Filed: Sep. 11, 2002

(65) Prior Publication Data

US 2003/0144257 A1 Jul. 31, 2003

Related U.S. Application Data

(63) Continuation-in-part of application No. 10/200,364, filed on Jul. 22, 2002, which is a continuation-in-part of application No. 10/067,010, filed on Feb. 4, 2002, which is a continuation-in-part of application No. 09/958,050, filed as application No. PCT/GB01/03495 on Aug. 3, 2001.

(30) Foreign Application Priority Data

Aug. 5, 2000 (GB) ................................................ 0019172

(51) Int. Cl.$^7$ .......................... A61K 31/58; C07J 17/00
(52) U.S. Cl. ...................................... 514/172; 540/114
(58) Field of Search ........................... 514/172; 540/114

(56) References Cited

U.S. PATENT DOCUMENTS

| | | | |
|---|---|---|---|
| 3,067,197 A | 12/1962 | Agnello et al. |
| 3,639,434 A | 2/1972 | Oxley et al. |
| 3,828,080 A | 8/1974 | May et al. |
| 3,856,828 A | 12/1974 | Phillips et al. |
| 3,981,894 A | 9/1976 | Phillipps et al. |
| 3,989,686 A | 11/1976 | Phillipps et al. |
| 4,093,721 A | 6/1978 | Phillipps et al. |
| 4,187,301 A | 2/1980 | Edwards |
| 4,188,385 A | 2/1980 | Edwards |
| 4,198,403 A | 4/1980 | Alvarez |
| 4,261,984 A | 4/1981 | Alvarez |
| 4,263,289 A | 4/1981 | Edwards |
| 4,267,173 A | 5/1981 | Draper |
| 4,285,937 A | 8/1981 | Kalvoda |
| 4,310,466 A | 1/1982 | Edwards |
| 4,335,121 A | 6/1982 | Phillipps et al. |
| 4,377,575 A | 3/1983 | Stache et al. |
| 4,472,393 A | 9/1984 | Shapiro |
| 4,607,028 A | 8/1986 | Schmidlin |
| 4,710,495 A | 12/1987 | Bodor |
| 4,861,765 A | 8/1989 | Mitsukuchi et al. |
| 4,992,474 A | 2/1991 | Skidmore et al. |
| 4,994,439 A | 2/1991 | Longnecker et al. |
| 4,996,335 A | 2/1991 | Bodor |
| 5,250,293 A | 10/1993 | Gleich |
| 5,420,120 A | 5/1995 | Boltralik |
| 5,658,549 A | 8/1997 | Akehurst et al. |
| 5,707,984 A | 1/1998 | Tjoeng et al. |
| 5,837,699 A | 11/1998 | Sequeira et al. |
| 5,849,265 A | 12/1998 | Li-Bovet et al. |
| 5,889,015 A | 3/1999 | Sequeira et al. |
| 5,919,776 A | 7/1999 | Hagmann et al. |
| 5,972,920 A | 10/1999 | Seidel |
| 5,981,517 A | 11/1999 | Bodor |
| 6,057,307 A | 5/2000 | Sequeira et al. |
| 6,127,353 A | 10/2000 | Yuen et al. |
| 6,136,294 A | 10/2000 | Adjei et al. |
| 6,197,761 B1 | 3/2001 | Biggadike et al. |
| 6,261,539 B1 | 7/2001 | Adjei et al. |
| 6,395,300 B1 | 5/2002 | Straub et al. |

FOREIGN PATENT DOCUMENTS

| | | |
|---|---|---|
| DE | 2336693 | 2/1975 |
| DE | 2538569 | 3/1977 |
| EP | 0004773 | 10/1979 |

(List continued on next page.)

OTHER PUBLICATIONS

Janette M. Mahoney et al., "Drug effects on the neovascularization response to silver nitrate cauterization of the rat cornea" Current Eye Research, vol. 4, No. 5, 1985, pp. 531–535.

(List continued on next page.)

Primary Examiner—Barbara P. Badio
(74) Attorney, Agent, or Firm—James P. Riek

(57) ABSTRACT

There is provided a crystalline chemical composition comprising a compound of formula (I)

in which the crystal lattice is stabilised by the presence of a guest molecule, characterised in the crystalline composition is of space group $P2_12_12_1$ having unit cell dimensions of about 7.6±0.6 Å, 12.7±0.7 Å, and 33±3 Å when determined at 120K.

16 Claims, 8 Drawing Sheets

FOREIGN PATENT DOCUMENTS

| | | |
|---|---|---|
| EP | 0057401 | 8/1982 |
| EP | 0135476 | 3/1985 |
| EP | 0179583 | 4/1986 |
| EP | 0416951 | 3/1991 |
| EP | 0418716 | 3/1991 |
| EP | 0521455 | 1/1993 |
| EP | 0640616 | 3/1995 |
| EP | 0646593 | 4/1995 |
| FR | 580494 | 10/1986 |
| GB | 1384372 | 2/1975 |
| GB | 1438940 | 6/1976 |
| GB | 1517278 | 7/1978 |
| GB | 2079755 | 1/1982 |
| GB | 2140800 | 12/1984 |
| IL | 109656 | 2/1998 |
| JP | 04208267 | 7/1992 |
| WO | 92/14472 | 9/1992 |
| WO | 94/21229 | 9/1994 |
| WO | 95/31964 | 11/1995 |
| WO | 96/19199 | 6/1996 |
| WO | 97/05136 | 2/1997 |
| WO | 97/15298 | 5/1997 |
| WO | 97/24365 | 7/1997 |
| WO | 97/46243 | 12/1997 |
| WO | 98/17676 | 4/1998 |
| WO | 98/34596 | 8/1998 |
| WO | 98/43630 | 10/1998 |
| WO | 99/01467 | 1/1999 |
| WO | 99/25359 | 5/1999 |
| WO | 99/32089 | 7/1999 |
| WO | 00/16814 | 3/2000 |
| WO | 00/33892 | 6/2000 |
| WO | 00/38811 | 7/2000 |
| WO | 00/57401 | 8/2000 |
| WO | 01/04118 | 1/2001 |
| WO | 01/15744 | 3/2001 |
| WO | 01/20331 | 3/2001 |
| WO | 01/54664 | 8/2001 |
| WO | 01/62722 | 8/2001 |
| WO | 01/78736 | 10/2001 |
| WO | 01/78739 | 10/2001 |
| WO | 01/78741 | 10/2001 |
| WO | 01/78745 | 10/2001 |
| WO | 02/00199 | 1/2002 |
| WO | 02/00679 | 1/2002 |
| WO | 02/007767 | 1/2002 |
| WO | 02/008243 | 1/2002 |
| WO | 02/01368 | 2/2002 |
| WO | 02/012265 | 2/2002 |
| WO | 02/012266 | 2/2002 |
| WO | 02/26723 | 4/2002 |
| WO | 02/053186 | 7/2002 |
| WO | 02/066422 | 8/2002 |
| WO | 02/070490 | 9/2002 |
| WO | 02/076933 | 10/2002 |
| WO | 02/085296 | 10/2002 |
| WO | 02/088167 | 11/2002 |
| WO | 02/100879 | 12/2002 |
| WO | 03/013427 | 2/2003 |
| WO | 03/033000 | 4/2003 |
| WO | 03/035668 | 5/2003 |
| WO | 03/040691 | 5/2003 |
| WO | 03/042229 | 5/2003 |
| WO | 03/042230 | 5/2003 |
| ZA | 872389 | 4/1987 |

OTHER PUBLICATIONS

Richard A. Kenley et al., "An Automated, Column–Switching HPLC Method for Analyzing Active and Excipient Materials in Both Cream and Ointment Formulations," Drug Development and Industrial Pharmacy, vol. 11 (9&10), 1985, pp. 1781–1796.

R. Woodford et al., "Activity and bioavailability of a new steroid (Timobesone acetate) in cream and ointment compared with Lidex and Dermovate creams and ointments and Betnovate cream" Int'l Journal of Pharmaceutics, vol. 26 (1985) pp. 145–155.

Denis J. Kertesz et al., "Thiol Esters from Steroid 17β–Carboxylic Acids: Carboxylate Activation and Internal Participation by 17 α–Acylates" J. Org. Chem., vol. 51, 1986, pp. 2315–2328.

Popper, T.L., et al., "Structure–Activity Relationship of a series of novel topical corticosteroids", Journal of Steroid Biochemistry 1987, 837–843.

John T. H. Ong et al., "Micellar Solubilization of Timobesone Acetate in Aqueous and Aqueous Propylene Glycol Solutions of Nonionic Surfactants", Pharmaceutical Research, vol. 5, No. 11, 1988, pp. 704–708.

John T. H. Ong et al., Intrinsic Potencies of Novel Thiol Esters Corticosteroids RS–85095 and RS–21314 as Compared With Clobetasol 17–Propionate and Fluocinonide Arch Dermatol, vol. 125, Dec. 1989, pp. 1662–1665.

Isogai, Mitsutaka, et al., "Binding affinities of Mornetasone Furoate and related compounds including its Metabolites for the Glucocorticoid Receptor of Rat Skin Tissue" J. Steroid Biochem. Mol. Biol., 1993, 141–145.

S.J. Lane et al., "Evaluation of a New Capillary Electrochromatography/Mass Spectrometry Interface Using Short Columns and High Field Strengths for Rapid and Efficient Analyses," Rapid Communications in Mass Spectrometry, vol. 10, 1996, pp. 733–736.

Franklin I. Aigbirhio et al., "Automated Radiosynthesis of No–carrier–added [S–fluoromethyl–$^{18}$F]Fluticasone Propionate as a Radiotracer for Lung Deposition Studies with PET" Journal Labeled Compounds and Radiopharmaceuticals vol. 39, No. 7, 1997, pp. 569–584.

Nisha Mistry et al., "Characterisation of Impurities in bulk drug batches of fluticasone propionate using directly coupled HPLC–NMR spectroscopy and HPLC–MS," Journal of Pharmaceutical and Biomedical Analysis vol. 16, 1997, pp. 697–705.

Nisha Mistry et al., Impurity profiling in bulk pharmaceuticals batches using 19F NMR spectroscopy and distinction between monomeric and dimeric impurities by NMR–based diffusion measurements, Journal of Pharmaceutical and Biomedical Analysis, vol. 19, 1999, pp. 511–517.

N. Smith et al., "Comparison of the electroosmotic flow profiles and selectivity of stationary phases used in capillary electrochromatography," Journal of Chromatography A., vol. 832, 1999, pp. 44–54.

R.C. Garner et al., "A validation study comparing accelerator MS and liquid scintillation counting for analysis of $^{14}$C–labelled drugs in plasma, urine and faecal extracts", Journal of Pharmaceutical and Biomedical Analysis vol. 24, 2000, pp. 197–209.

Harold S. Nelson et al. "Fluticasone propionate/salmeterol combination provides more effective asthma control than low–dose inhaled corticosteroid plus montelukast," J. Allergy Clin. Immunol., vol. 106, No. 6, Dec. 2000, pp. 1088–1095.

Gunnar Johansson et al., "Comparison of Salmeterol/Fluticasone Propionate Combination With Budesonide in Patients With Mild–to–Moderate Asthma" Clin. Drug Invest. vol. 21, No. 9, 2001, pp. 633–642.

Bertil Pettersson et al., Re–evaluation of the classical *Mycoplasma lipophilum* cluster (Welsburg et al. 1989) and description of two new clusters in the hominis group based on 16S rDNA sequences, Int'l Journal of Systematic & Evolutionary Microbiology vol. 51, 2001, pp. 633–643.

Sarah A. Lewis et al., "Association of specific allergen sensitization with socioeconomic factors and allergic disease in a population of Boston women", J. Allergy Clin. Immunol., vol. 107, No. 4, Apr. 2001, pp. 615–622.

Katherine A. Lyseng–Williamson et al., "Inhaled Salmeterol/Fluticasone Propionate Combination in Chronic Obstructive Pulmonary Disease," Am. J. Respir. Med. vol. 1, No. 4, 2002, pp. 273–282.

Jeffrey W. Millard et al., "Solubilization by cosolvents Establishing useful constants for the log–linear model," Int'l Journal of Pharmaceutics vol. 245, 2002, pp. 153–166.

C. Baumgarten et al., "Initial Treatment of Symptomatic Mild to Moderate Bronchial Asthma with the Salmeterol/ Fluticasone Propionate (50/250µg) Combination Product (SAS 40023)" European Journal of Medical Research vol. 7, 2002, pp. 1–7.

Stephen J. Fowler et al., "Step–down therapy with low–dose fluticasone–salmeterol combination or medium–dose hydrofluoroalkane 134a–beclomethasone alone" J. Allergy Clin. Immunol., vol. 109, No. 6, Jun. 2002, pp. 929–935.

Elizabeth F. Juniper et al., "Impact of Inhaled Salmeterol/ Fluticasone Propionate Combination Product versus Budesonide on the Health–Related Quality of Life of Patients with Asthma," Am. J. Respir. Med., vol. 1, No. 6, 2002, pp. 435–440.

William Busse et al., "Steroid–sparing effects of fluticasone propionate 100 µg and salmeterol 50 µg administered twice daily in a single product in patients previously controlled with fluticaasone propionate 250 µg administered twice daily"J. Allergy Clin. Immunol., vol. 111, No. 1, Jan. 2003, pp. 57–65.

Ueno H et al., "Synthesis and Evaluation of Antiinflammatory activities of a Series of Corticosteroid 17. Alpha –Esters Containing a Functional Group" ,Journal of Medicinal Chemistry, American Chemical Society, vol. 34, No. 8, Aug. 1991, pp. 2468–2473.

Peter J Barnes, "Novel approaches and targets for treatment of Chronic Obstructive Pulmonary Disease" American Journal of Respiratory and Critical Care Medicine, vol. 160, 1999, pp. S72–S79.

B.J O Conner: "Combination Therapy", Pulmonary Pharmacology and Therapeutics, vol. 11, No. 5/6, 1998, pp. 397–399.

Peter J Barnes, "Chronic Obstructive Pulmonary Disease: new opportunities for drug development" Trends in Pharmacological Sciences, Elsevenir Trends Journal, vol. 19, No. 10, 1998, pp. 415–423.

Simon Bowler,"Long acting beta agonists" , Austrailian Family Physician,vol. 27 , No. 12, 1998, pp. 1114–1118.

Naedle–Risha R et al, "Dual components of optimal asthma therapy: scientific and clinical rationale for the use of long acting beta–agonists with inhaled corticosteroidsd", The Journal of the American Osteopathic Association, vol. 101, No. 9 , Sep. 2001, pp. 2001–2009.

T Van Der Molen et al., "Effects of the Long Acting Beta Agonist Formoterol on Asthma Control in Asthmatic Patients Using Inhaled Corticosteroids", vol. 52, No. 6, 1997, pp. 535–539.

B.N. Lutsky et al, "A Novel Class of potent Topical Anti–Inflammatory Agents: 17 Benzoylated, 7—Halogeno Substituted Corticosteroids", Arzeneimittel Forschung, vol. 29, No. 11, Nov. 1979, pp. 1662–1667.

Peter J. Barnes, "Efficacy of Inhaled Corticosteroids in Asthma", The Journal of Allergy and Clinical Immunology, vol. 102, No. 4, pp. 531–538.

US Publication No. 2002/0081266 publ. on Jun. 27, 2002.
US Publication No. 2002/0103392 publ. on Aug. 01, 2002.
US Publication No. 2002/0165211 publ. on Nov. 07, 2002.
US Publication No. 2002/0173496 publ. on Nov. 21, 2002.
US Publication No. 2002/0177581 publ. on Nov. 28, 2002.
US Publication No. 2003/0073676 publ. on Apr. 17, 2003.
US Publication No. 2003/0109511 publ. on Jun. 12, 2003.
US Publication No. 2003/0144257 publ. on Jul. 31, 2003.
US Publication No. 2003/0158163 publ. on Aug. 21, 2003.

Phillipps, G.H., et al., "Synthesis and Structure–Activity Relationships in a series of Antiinflammatory Corticosteroid Analogues, Halomethyl Androstane–17β–carbothioates and– 17β–carboselenoates," Journal of Medicinal Chemistry 1994, 37, 3717–3729.

Knobil, K., et al., "Adding Salmeterol is More Effective Than Increasing the Dose of Fluticasone for Patients With Asthma who are Symptomatic on Low Dose Fluticasone," European Respiratory Review, Copenhagen, DK, vol. 12, No. Suppl 29, Dec. 1998, pp. 19S–20S, XP000992769.

Shapiro, E.L., et. al, "17 Heteroaroyl Esters of Corticosteroids 2. 11–Beta Hydroxy Series," Journal of Medicinal Chemistry, American Chemical Society, Washington, US, vol. 30, No. 9, 1987, pp. 1581–1588, XP002153839.

US patent application No.: 09/958,050 filed on Oct. 02, 2001.
US patent application No.: 10/066,836 filed on Feb. 04, 2002.
US patent application No.: 10/066,951filed on Feb. 04, 2002.
US patent application No.: 10/066,964 filed on Feb. 04, 2002.
US patent application No.: 10/067,101 filed on Feb. 04, 2002.
US patent application No.: 10/087,020 filed on Feb. 04, 2002.
US patent application No.: 10/200,364 filed on Jul. 22, 2002.
US patent application No.: 10/281,735 filed on Oct. 28, 2002.

ANTI-INFLAMMATORY ANDROSTANE DERIVATIVE COMPOSITIONS

CROSS REFERENCE TO RELATED APPLICATIONS

This application is a Continuation-in-part of U.S. patent application Ser. No. 10/200,364 filed Jul. 22, 2002 which is a Continuation-in-part of U.S. patent application Ser. No. 10/067,010, filed Feb. 4, 2002 which is a Continuation-in-part of U.S. patent application Ser. No. 09/958,050 filed Oct. 2, 2001, which is 35 USC 371 filing of International Patent Application No. PCT/GB01/03495 filed Aug. 3, 2001, which claims priority to United Kingdom Patent Application No. GB 0019112.6 filed Aug. 5, 2000.

FIELD OF THE INVENTION

The present invention relates to a novel composition containing an anti-inflammatory and anti-allergic compound of the androstane series and to processes for its preparation. The present invention also relates to pharmaceutical formulations containing the composition and to therapeutic uses thereof, particularly for the treatment of inflammatory and allergic conditions.

BACKGROUND OF THE INVENTION

Glucocorticoids which have anti-inflammatory properties are known and are widely used for the treatment of inflammatory disorders or diseases such as asthma and rhinitis. For example, U.S. Pat. No. 4,335,121 discloses 6α,9α-Difluoro-17α-(1-oxopropoxy)-11β-hydroxy-16α-methyl-3-oxo-androsta-1,4-diene-17β-carbothioic acid S-fluoromethyl ester (known by the generic name of fluticasone propionate) and derivatives thereof. The use of glucocorticoids generally, and especially in children, has been limited in some quarters by concerns over potential side effects. The side effects that are feared with glucocorticoids include suppression of the Hypothalamic-Pituitary-Adrenal (HPA) axis, effects on bone growth in children and on bone density in the elderly, ocular complications (cataract formation and glaucoma) and skin atrophy. Certain glucocorticoid compounds also have complex paths of metabolism wherein the production of active metabolites may make the pharmacodynamics and pharmacokinetics of such compounds difficult to understand. Whilst the modern steroids are very much safer than those originally introduced, it remains an object of research to produce new molecules which have excellent anti-inflammatory properties, with predictable pharmacokinetic and pharmacodynamic properties, with an attractive side effect profile, and with a convenient treatment regime.

SUMMARY OF THE INVENTION

We have now identified a novel glucocorticoid compound and a crystalline composition thereof which substantially meets these objectives.

Thus, according to one aspect of the invention, there is provided a crystalline chemical composition comprising a compound of formula (I)

(I)

in which the crystal lattice is stabilised by the presence of a guest molecule, characterised in the crystalline composition is of space group $P2_12_12_1$ having unit cell dimensions of about 7.7±0.6 Å, 13.7±0.7 Å, and 37±3 Å when determined at 120K (hereinafter "a composition of the invention").

In the composition of the invention the crystalline lattice is stabilised by a hydrogen bonding interaction between the hydrogen atom of the C11 hydroxy on the compound of formula (I) with the oxygen of the C3 carbonyl on a second molecule of the compound of formula (I).

The nature of the crystal lattice can be seen by reference to FIG. 1 which shows the spacial arrangement of 4 molecules of steroid and 8 guests within a single unit cell for an example composition. Detail of the hydrogen bond interaction between the steroid molecules is shown in FIG. 3. FIG. 2 shows the conformation of the steroid molecule with 2 guest molecules present.

We have determined the XRPD profiles for a number of compositions according to the invention. These XRPD profiles are also apparently characteristic of the crystalline composition according to the invention. In particular they exhibit one or more of the following 3 features when determined at ambient temperature (eg around 295K):

(a) A peak in the range of around 4.3–5.0.
(b) A peak in the range of around 6.6–6.9.
(c) A peak in the range of around 11.5–11.8.

Typically they exhibit 2 or more of the above 3 features, especially 3 of the above features.

The XRPD profiles of compositions of the invention when crystallographically pure also preferably exhibit one or more of the following 6 features when determined at ambient temperature (eg around 295K):

(a) Absence of a peak at around 7.3 (eg around 7.1–7.5) which is associated with the profile of unsolvated Form 1, 2 and 3 polymorphs;
(b) Absence of a peak at around 7.5 (eg around 7.2–7.7) which is associated with the profile of another class of compositions of compound of formula (I);
(c) Absence of a peak at around 12.5 (eg around 12.3–12.7) which is associated with the profile of unsolvated Form 1, 2 and 3 polymorphs;
(d) Absence of a peak at around 8.8–9.6 which is associated with the profile of another class of compositions of compound of formula (I);
(e) Absence of a peak at around 10.5–11.1 which is associated with the profile of another class of compositions of compound of formula (I);
(f) Absence of a peak at around 12.2–12.6 which is associated with the profile of another class of compositions of compound of formula (I).

Preferably one or more preferably both of features (a) and (b) at least are exhibited. Preferably 3 or more preferably 4, especially 5, most especially all 6 of the above 6 features are exhibited.

The chemical name of the compound of formula (I) is 6α,9α-Difluoro-17α-[(2-furanylcarbonyl)oxy]-11β-hydroxy-16α-methyl-3-oxo-androsta-1,4-diene-17β-carbothioic acid S-fluoromethyl ester.

The compound of formula (I) and compositions thereof have potentially beneficial anti-inflammatory or anti-allergic effects, particularly upon topical administration, demonstrated by, for example, its ability to bind to the glucocorticoid receptor and to illicit a response via that receptor, with long acting effect. Hence, the compound of formula (I) and compositions thereof is useful in the treatment of inflammatory and/or allergic disorders, especially in once-per-day therapy.

Space group $P2_12_12_1$ is characterised by angles of 90° being present in each of the 3 axes.

We have discovered that the compound of formula (I) can form a crystalline composition of characteristic space group, unit cell dimensions and crystalline structure as evidenced by X-ray diffraction with a number of guest molecules.

The guest molecule preferably has a relative molecular weight in the range 16 to 150, more preferably 60 to 130, especially 70 to 120. Preferably the guest molecule is a liquid at ambient temperature and pressure (eg 295K, 1.013× $10^5$ Pa). However guest molecules which are a liquid under pressure may also be capable of acting as a guest molecule (especially under pressurised conditions). Substances which are solids at ambient temperature and pressure are also included.

Examples of suitable guest molecules include solvents e.g.:

Aromatic compounds eg benzene and substituted derivatives, especially benzene substituted with one or more (eg 1 or 2) halogen or $C_{1-4}$alkyl groups, for example toluene, o-xylene, m-xylene, fluorobenzene, chlorobenzene, ethylbenzene.

Preferred guest molecules are pharmaceutically acceptable substances and, as described below, compositions of the invention containing them may be used in therapy. However even if the guest molecule is not pharmaceutically acceptable then such compositions may be useful in the preparation of other compositions containing compound of formula (I), for example, other compositions of the invention containing guest molecules that are pharmaceutically acceptable or compound of formula (I) in unsolvated form.

The stoichiometry of the composition will usually be such that the ratio of compound to formula (I) to guest molecule, in molar terms, is 1:5–0.25, preferably 1:3.0–0.3, more preferably 1:2.2–0.6, especially 1: 2.2–0.8.

Unusually a composition of the invention has a crystal structure which is quite distinct from that of compound of formula (I) in the absence of a guest molecule, eg. the compound of formula (I) as unsolvated polymorph Form 1 which has a space group of $P2_1$ (i.e. two of the axis angles are 90°) and cell dimensions of 7.6, 14.1, 11.8 Å when determined at 150K. Thus if the guest molecule is removed below a threshold level (which will differ from guest to guest) for example by heating (optionally at reduced pressure eg under vacuum) then the crystal structure of the composition starts to break down and converts to that of the structure of an unsolvated compound of formula (I), typically unsolvated polymorph Form 2 or 3.

Preferably the unit cell dimentions are about 7.7±0.4 Å, 13.8±0.3 Å, and 36.8±3 Å when determined at 120K. Usually the unit cell dimensions are about 7.7±0.2 Å, 13.8±0.2 Å, and 36.8±2.7 Å when determined at 120K.

Table 1 shows the unit cell dimensions and peak positions for a number of example compositions:

TABLE 1

| Guest molecule | Unit cell dimensions | | | Peak positions | | |
|---|---|---|---|---|---|---|
| Toluene | 7.8 | 13.7 | 34.2 | 4.9 | 6.8 | 11.8 |
| m-xylene | 7.8 | 13.8 | 35.9 | 4.8 | 6.8 | 11.5 |
| o-xylene | ND | ND | ND | 5.0 | 6.9 | 11.7 |
| fluorobenzene | 7.7 | 13.9 | 38.7 | ND | ND | ND |
| ethylbenzene | 7.7 | 13.8 | 37.8 | ND | ND | ND |
| chlorobenzene | 7.8 | 13.7 | 39.3 | 4.3 | 6.6 | — |

ND = not determined

Compound (I) undergoes highly efficient hepatic metabolism to yield the 17-β carboxylic acid (X) as the sole major metabolite in rat and human in vitro systems. This metabolite has been synthesised and demonstrated to be >1000 fold less active than the parent compound in in vitro functional glucocorticoid assays.

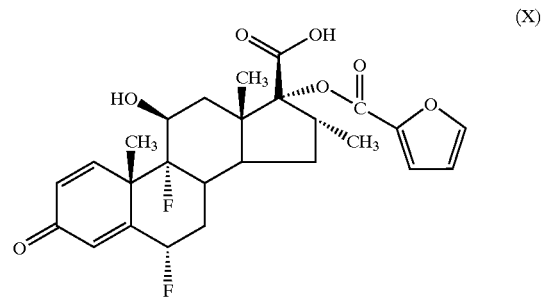

(X)

This efficient hepatic metabolism is reflected by in vivo data in the rat, which have demonstrated plasma clearance at a rate approaching hepatic blood flow and an oral bioavailability of <1%, consistent with extensive first-pass metabolism.

In vitro metabolism studies in human hepatocytes have demonstrated that compound (I) is metabolised in an identical manner to fluticasone propionate but that conversion of (I) to the inactive acid metabolite occurs approximately 5-fold more rapidly than with fluticasone propionate. This very efficient hepatic inactivation would be expected to minimise systemic exposure in man leading to an improved safety profile.

Inhaled steroids are also absorbed through the lung and this route of absorption makes a significant contribution to systemic exposure. Reduced lung absorption could therefore provide an improved safety profile. Studies with compound (I) have shown significantly lower exposure to compound (I) than with fluticasone propionate after dry powder delivery to the lungs of anaesthetised pigs.

An improved safety profile is believed to allow the compound of formula (I) to demonstrate the desired anti-inflammatory effects when administered once-per day. Once-per-day dosing is considered to be significantly more convenient to patients than the twice-per day dosing regime that is normally employed for fluticasone propionate.

Examples of disease states in which the compound of formula (I) and compositions thereof have utility include skin diseases such as eczema, psoriasis, allergic dermatitis, neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

The compound of formula (I) may also have use in the treatment of conjunctiva and conjunctivitis.

The composition of the invention is expected to be most useful in the treatment of inflammatory disorders of the respiratory tract e.g. asthma, COPD and rhinitis particularly asthma and rhinitis.

It will be appreciated by those skilled in the art that reference herein to treatment extends to prophylaxis as well as the treatment of established conditions.

As mentioned above, the composition of the invention is useful in human or veterinary medicine, in particular as an anti-inflammatory and anti-allergic agent.

There is thus provided as a further aspect of the invention the composition of the invention for use in human or veterinary medicine, particularly in the treatment of patients with inflammatory and/or allergic conditions, especially for treatment once-per-day.

According to another aspect of the invention, there is provided the use of the composition of the invention for the manufacture of a medicament for the treatment of patients with inflammatory and/or allergic conditions, especially for treatment once-per-day.

In a further or alternative aspect, there is provided a method for the treatment of a human or animal subject with an inflammatory and/or allergic condition, which method comprises administering to said human or animal subject an effective amount of the composition of the invention, especially for administration once-per-day.

The composition of the invention may be formulated for administration in any convenient way, and the invention therefore also includes within its scope pharmaceutical compositions comprising the composition of the invention together, if desirable, in admixture with one or more physiologically acceptable diluents or carriers. Pharmaceutical compositions suitable for once-per-day administration are of particular interest.

Further, there is provided a process for the preparation of such pharmaceutical compositions which comprises mixing the ingredients.

The composition of the invention may, for example, be formulated for oral, buccal, sublingual, parenteral, local or rectal administration, especially local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

Advantageously compositions for topical administration to the lung include dry powder compositions and spray compositions.

Dry powder compositions for topical delivery to the lung by inhalation may, for example, be presented in capsules and cartridges for use in an inhaler or insufflator of, for example, gelatine. Formulations generally contain a powder mix for inhalation of the compound of the invention and a suitable powder base (carrier substance) such as lactose or starch. Use of lactose is preferred. Each capsule or cartridge may generally contain between 20 $\mu$g–10 mg of the compound of formula (I) in a composition of the invention optionally in combination with another therapeutically active ingredient. Alternatively, the composition of the invention may be presented without excipients. Packaging of the formulation may be suitable for unit dose or multi-dose delivery. In the case of multi-dose delivery, the formulation can be pre-metered (e.g. as in Diskus, see GB 2242134 or Diskhaler, see GB 2178965, 2129691 and 2169265) or metered in use (e.g. as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a composition of the invention preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Pharmaceutical formulations which are non-pressurised and adapted to be administered as a dry powder topically to the lung via the buccal cavity (especially those which are free of excipient or are formulated with a diluent or carrier such as lactose or starch, most especially lactose) are of particular interest.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the composition of the invention optionally in combination with another therapeutically active ingredient and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol. One example formulation is excipient free and consists essentially of (e.g. consists of) composition of the invention (optionally together with a further active ingredient) and a propellant selected from 1,1,1,2-tetrafluoroethane, 1,1,1,2,3,3,3-heptafluoro-n-propane and mixture thereof. Another example formulation comprises particulate composition of the invention, a propellant selected from 1,1,1,2-tetrafluoroethane, 1,1,1,2,3,3, 3-heptafluoro-n-propane and mixture thereof and a suspending agent which is soluble in the propellant e.g. an oligolactic acid or derivative thereof as described in WO94/21229. The preferred propellant is 1,1,1,2-tetrafluoroethane. Pressurised formulations will generally be retained in a canister (e.g. an aluminium canister) closed with a valve (e.g. a metering valve) and fitted into an actuator provided with a mouthpiece.

Medicaments for administration by inhalation desirably have a controlled particle size. The optimum particle size for inhalation into the bronchial system is usually 1–10 $\mu$m, preferably 2–5 $\mu$m. Particles having a size above 20 $\mu$m are generally too large when inhaled to reach the small airways. To achieve these particle sizes the particles of the composition of the invention as produced may be size reduced by conventional means e.g. by micronisation. The desired fraction may be separated out by air classification or sieving. Preferably, the particles will be crystalline, prepared for example by a process which comprises mixing in a continuous flow cell in the presence of ultrasonic radiation a flowing solution of compound of formula (I) as medicament in a liquid solvent with a flowing liquid antisolvent for said medicament (e.g. as described in International Patent Application PCT/GB99/04368) or else by a process which comprises admitting a stream of solution of the substance in a liquid solvent and a stream of liquid antisolvent for said substance tangentially into a cylindrical mixing chamber having an axial outlet port such that said streams are thereby intimately mixed through formation of a vortex and precipitation of crystalline particles of the substance is thereby caused (e.g. as described in International Patent Application PCT/GB00/04327).

When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60–90 μm and not less than 15% will have a MMD of less than 15 μm.

Formulations for administration topically to the nose (e.g. for the treatment of rhinitis) include pressurised aerosol formulations and aqueous formulations administered to the nose by pressurised pump. Formulations which are non-pressurised and adapted to be administered topically to the nasal cavity are of particular interest. The formulation preferably contains water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

Other possible presentations include the following:

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

If appropriate, the formulations of the invention may be buffered by the addition of suitable buffering agents.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1% and preferably 0.01 to 0.5%. However, in powders for inhalation or insufflation the proportion used will usually be within the range of from 0.1 to 5%.

Aerosol formulations are preferably arranged so that each metered dose or "puff" of aerosol contains 1 μg–2000 μg e.g. 20 μg–2000 μg, preferably about 20 μg–500 μg of compound of formula (I) optionally in combination with another therapeutically active ingredient. Administration may be once daily or several times daily, for example 2, 3, 4 or 8 times, giving for example 1, 2 or 3 doses each time. Preferably the composition of the invention is delivered once or twice daily. The overall daily dose with an aerosol will typically be within the range 10 μg–10 mg e.g. 100 μg–10 mg preferably, 200 μg–2000 μg.

Topical preparations may be administered by one or more applications per day to the affected area; over skin areas occlusive dressings may advantageously be used. Continuous or prolonged delivery may be achieved by an adhesive reservoir system.

For internal administration the compound according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms i.e. tablets and capsules. Such dosage unit forms contain from 0.1 mg to 20 mg preferably from 2.5 to 10 mg of the compound of formula (I).

The compound according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5–30 mg, dependent on the condition being treated, and the duration of treatment desired.

Slow release or enteric coated formulations may be advantageous, particularly for the treatment of inflammatory bowel disorders.

Since the compound of formula (I) is long-acting, preferably the composition of the invention will be delivered once-per-day and the dose will be selected so that the compound has a therapeutic effect in the treatment of respiratory disorders (e.g. asthma or COPD, particularly asthma) over 24 hours or more.

The pharmaceutical compositions according to the invention may also be used in combination with another therapeutically active agent, for example, a $\beta_2$ adrenoreceptor agonist, an anti-histamine or an anti-allergic. The invention thus provides, in a further aspect, a combination comprising the composition of the invention together with another therapeutically active agent, for example, a $\beta_2$-adrenoreceptor agonist, an anti-histamine or an anti-allergic.

Examples of $\beta_2$-adrenoreceptor agonists include salmeterol (e.g. as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Pharmaceutical compositions employing combinations with long-acting $\beta_2$-adrenoreceptor agonists (e.g. salmeterol and salts thereof) are particularly preferred, especially those which have a therapeutic effect (e.g. in the treatment of asthma or COPD, particularly asthma) over 24 hours or more.

Since the compound of formula (I) is long-acting, preferably the composition comprising the compound of formula (I) and the long-acting $\beta_2$-adrenoreceptor agonists will be delivered once-per-day and the dose of each will be selected so that the composition has a therapeutic effect in the treatment of respiratory disorders effect (e.g. in the treatment of asthma or COPD, particularly asthma) over 24 hours or more.

Examples of anti-histamines include methapyrilene or loratadine.

Other suitable combinations include, for example, other anti-inflammatory agents e.g. NSAIDs (e.g. sodium cromoglycate, nedocromil sodium, PDE4 inhibitors, leukotriene antagonists, iNOS inhibitors, tryptase and elastase inhibitors, beta-2 integrin antagonists and adenosine 2a agonists)) or antiinfective agents (e.g. antibiotics, antivirals).

Also of particular interest is use of the composition of the invention in combination with a phosphodiesterase 4 (PDE4) inhibitor e.g. cilomilast or a salt thereof.

The combination referred to above may conveniently be presented for use in the form of a pharmaceutical formulation and thus pharmaceutical formulations comprising a combination as defined above together with a physiologically acceptable diluent or carrier represent a further aspect of the invention.

The compound according to the invention in combination with another therapeutically active ingredient as described above may be formulated for administration in any convenient way, and the invention therefore also includes within its scope pharmaceutical formulations comprising the composition of the invention in combination with another therapeutically active ingredient together, if desirable, in admixture with one or more physiologically acceptable diluents or carriers. The preferred route of administration for inflammatory disorders of the respiratory tract will generally be administration by inhalation.

Further, there is provided a process for the preparation of such pharmaceutical compositions which comprises mixing the ingredients.

Therapeutic agent combinations may be in any form, for example combinations may comprise a single dose containing separate particles of individual therapeutics, and optionally excipient material(s), alternatively, multiple therapeutics may be formed into individual multicomponent particles, formed for example by coprecipitation, and optionally containing excipient material(s).

The individual compounds of such combinations may be administered either sequentially in separate pharmaceutical compositions as well as simultaneously in combined pharmaceutical formulations. Appropriate doses of known therapeutic agents will be readily appreciated by those skilled in the art.

The composition of the invention may be prepared by the methodology described hereinafter, constituting a further aspect of this invention.

A first process for preparing a composition of the invention comprises crystallising the composition from a solution containing a compound of formula (I) and the guest molecule. The solution containing the guest molecule could be the guest itself when this a liquid, or could be the guest dissolved in another liquid substance which substance does not act as a guest molecule.

Optionally, for better control and reproduceability, the crystallisation process may be assisted by seeding with crystals of the composition of the invention. The seed crystals of the composition of the invention need not contain the same guest molecule.

A second process for preparing a composition of the invention comprises contacting the compound of formula (I) or a composition according to the invention thereof in solid form with a liquid containing the guest molecule (for example by slurrying) and obtaining the composition therefrom. The liquid containing the guest molecule could be the guest itself when this a liquid, or could be the guest dissolved in another liquid substance which substance does not act as a guest molecule.

A third process for preparing a composition of the invention comprises contacting a compound of formula (I) or a composition according to the invention thereof in solid form with a vapour containing the guest molecule. This process is suitable when the guest has acceptable volatility e.g. when the guest is a solvent.

In the second and third processes, the compound of formula (I) may be employed in the form of a composition with a guest molecule or in a form without a guest molecule (eg as unsolvated polymorph Form 1, 2 or 3). In the first process the compound of formula (I) or a composition according to the invention may be dissolved in the solution or prepared in situ.

In one particular embodiment of this aspect of the invention the input compound of formula (I) in the first, second and third processes is in the form of a substantially amorphous solid. Preferably the compound of formula (I) in the form of a substantially amorphous solid is preferably in the form of substantially amorphous particles. For example the the compound of formula (I) in the form of substantially amorphous particles may be obtained by spray drying a solution containing the compound of formula (I). Any solvent that will dissolve the compound of formula (I) that can be evaporated safely in a spray drying process may be used. Suitable solvents for forming the solution include, but are not limited to, methyl acetate, ethyl acetate, isopropyl acetate, acetone, 2-butanone, 3-pentanone, 4-methyl-2-pentanone, ethanol, methanol, 1-propanol, propan-2-ol, acetonitrile, chloroform, dichloromethane especially methylethylketone (2-butanone). Solution concentration will typically be 0.5–50% specifically 10–40% eg 20–30%. Lower concentrations may be more suitable for preparing smaller particle sizes especially 2–4% e.g. 3.5–4%. The concentration that may be employed will be limited by the dissolution power of the solvent. Methylethylketone is preferred since it dissolves compound of formula (I) at a relatively high concentration which results in production advantages. The compound of formula (I) may be employed in non-solvated form or in the form of a composition of the invention (e.g. with acetone). Preferably it is employed as the non-solvated Form 1 polymorph. Spray drying maybe performed, for example, using apparatus supplied by Buchi or Niro. A pneumatic spray nozzle orifice of e.g. 0.04 inches is suitable, although alternate atomization methods such as rotary and pressure nozzles can be used. Solution flow rate may typically be in the range 1–100 ml/min, especially 15–30ml/min. The inlet temperature and flow rate combi nation should be suitable to evaporate the solvent completely to minimize the risk of solvent trapped in the particle expediting an amorphous to crystalline transition. Inlet temperatures can range from 50–250° C., typically 100–200° C.

Compound of formula (I) in unsolvated form which is itself a useful substance has been found to exist in 3 crystalline polymorphic forms, Forms 1, 2 and 3, although Form 3 may be an unstable variant of Form 2. The Forms are characterised by their XRPD patterns shown in FIG. 8. Broadly speaking the Forms are characterised in their XRPD profiles by the absence of guest molecules and by peaks as follows:

Form 1: Peak at around 18.9 degrees 2Theta

Form 2: Peaks at around 18.4 and 21.5 degrees 2Theta

Form 3: Peaks at around 18.6 and 19.2 degrees 2Theta.

Forms 1 appears likely to be the thermodynamically most stable form since Forms 2 and 3 are converted into Form 1 on heating.

A process for preparing a compound of formula (I) as crystalline unsolvated Form 1 polymorph comprises dissolving compound of formula (I) in methylisobutylketone or ethyl acetate and producing compound of formula (I) as unsolvated Form 1 by addition of an anti-solvent such as iso-octane or toluene.

According to a first preferred embodiment of this process the compound of formula (I) may be dissolved in ethyl acetate and compound of formula (I) as unsolvated Form 1 polymorph may be obtained by addition of toluene as anti-solvent. In order to improve the yield, preferably the ethyl acetate solution is hot and once the toluene has been added the mixture is distilled to reduce the content of ethyl acetate.

According to a second preferred embodiment of this process the compound of formula (I) may be dissolved in methylisobutylketone and compound of formula (I) as crystalline unsolvated Form 1 polymorph may be obtained by addition of isooctane as anti-solvent.

A process for preparing a compound of formula (I) as unsolvated Form 2 polymorph comprises dissolving compound of formula (I) in unsolvated form in methanol or dry dichloromethane and recrystallising the compound of formula (I) as unsolvated Form 2 polymorph. Typically the compound of formula (I) will be dissolved in hot methanol or dry dichloromethane and allowed to cool.

A process for preparing a compound of formula (I) as unsolvated Form 3 polymorph comprises dissolving compound of formula (I) in particular as the composition with acetone in dichloromethane in the presence of water (typically 1–3% water by volume) and recrystallising the compound of formula (I) as unsolvated Form 3 polymorph.

As mentioned above, compositions of the invention may also find use as manufacturing intermediates in the preparation of compound of formula (I) in unsolvated form, or in the preparation of other compositions of the invention, or in pharmaceutical compositions thereof.

For example, a process for preparation of compound of formula (I) in unsolvated form (typically unsolvated polymorph Form 1) comprises removing the guest molecule from a composition of the invention.

A process for preparing a compound of formula (I) comprises alkylation of a thioacid of formula (II)

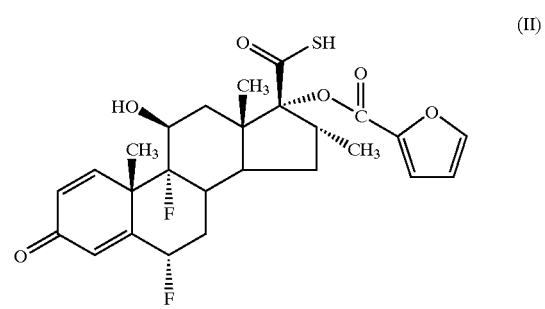

or a salt thereof.

In this process the compound of formula (II) may be reacted with a compound of formula $FCH_2L$ wherein L represents a leaving group (e.g. a halogen atom, a mesyl or tosyl group or the like) for example, an appropriate fluoromethyl halide under standard conditions. Preferably, the fluoromethyl halide reagent is bromofluoromethane. Preferably the compound of formula (II) is employed as a salt, particularly the salt with diisopropylethylamine.

In a preferred process for preparing the compound of formula (I), the compound of formula (II) or a salt thereof is treated with bromofluoromethane optionally in the presence of a phase transfer catalyst. A preferred solvent is methylacetate, or more preferably ethylacetate, optionally in the presence of water. The presence of water improves solubility of both starting material and product and the use of a phase transfer catalyst results in an increased rate of reaction. Examples of phase transfer catalysts that may be employed include (but are not restricted to) tetrabutylammonium bromide, tetrabutylammonium chloride, benzyltributylammonium bromide, benzyltributylammonium chloride, benzyltriethylammonium bromide, methyltributylammonium chloride and methyltrioctylammonium chloride. THF has also successfully been employed as solvent for the reaction wherein the presence of a phase transfer catalyst again provides a significantly faster reaction rate. Preferably the product present in an organic phase is washed firstly with aqueous acid e.g. dilute HCl in order to remove amine compounds such as triethylamine and diisopropylethylamine and then with aqueous base e.g. sodium bicarbonate in order to remove any unreacted precursor compound of formula (II).

Compounds of formula (II) may be prepared from the corresponding 17(X-hydroxyl derivative of formula (III):

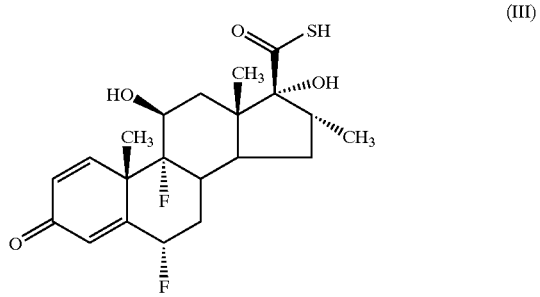

using for example, the methodology described by G. H. Phillipps et al., (1994) Journal of Medicinal Chemistry, 37, 3717–3729. For example the step typically comprises the addition of a reagent suitable for performing the esterification e.g. an activated derivative of 2-furoic acid such as an activated ester or preferably a 2-furoyl halide e.g. 2-furoyl chloride (employed in at least 2 times molar quantity relative to the compound of formula (III)) in the presence of an organic base e.g. triethylamine. The second mole of 2-furoyl chloride reacts with the thioacid moiety in the compound of formula (III) and needs to be removed e.g. by reaction with an amine such as diethylamine.

This method suffers disadvantages, however, in that the resultant compound of formula (II) is not readily purified of contamination with the by-product 2-furoyldiethylamide. We have therefore invented several improved processes for performing this conversion.

In a first such improved process we have discovered that by using a more polar amine such as diethanolamine, a more water soluble by-product is obtained (in this case 2-furoyldiethanolamide) which permits compound of formula (II) or a salt thereof to be produced in high purity since the by-product can efficiently be removed by water washing.

Thus we provide a process for preparing a compound of formula (II) which comprises:
(a) reacting a compound of formula (III) with an activated derivative of 2-furoic acid as in an amount of at least 2 moles of the activated derivative per mole of compound of formula (III) to yield a compound of formula (IIA)

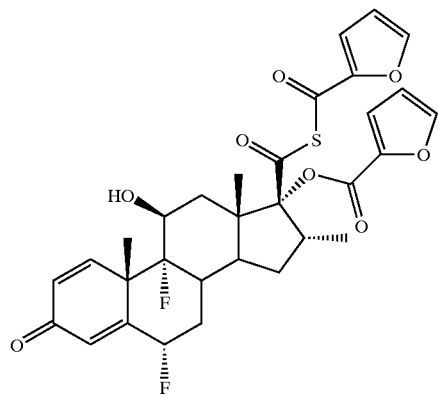

(IIA)

; and
(b) removal of the sulphur-linked 2-furoyl moiety from compound of formula (IIA) by reaction of the product of step (a) with an organic primary or secondary amine base capable of forming a water soluble 2-furoyl amide.

In two particularly convenient embodiments of this process we also provide methods for the efficient purification of the end product which comprise either
(c1) when the product of step (b) is dissolved in a substantially water immiscible organic solvent, purifying the compound of formula (II) by washing out the amide by-product from step (b) with an aqueous wash, or
(c2) when the product of step (b) is dissolved in a water miscible solvent, purifying the compound of formula (II) by treating the product of step (b) with an aqueous medium so as to precipitate out pure compound of formula (II) or a salt thereof.

In step (a) preferably the activated derivative of 2-furoic acid may be an activated ester of 2-furoic acid, but is more preferably a 2-furoyl halide, especially 2-furoyl chloride. A suitable solvent for this reaction is ethylacetate or methylacetate (preferably methylacetate) (when step (c1) may be followed) or acetone (when step (c2) may be followed). Normally an organic base e.g. triethylamine will be present.

In step (b) preferably the organic base is diethanolamine. The base may suitably be dissolved in a solvent e.g. methanol. Generally steps (a) and (b) will be performed at reduced temperature e.g. between 0 and 5° C. In step (c1) the aqueous wash may be water, however the use of brine results in higher yields and is therefore preferred. In step (c2) the aqueous medium is for example a dilute aqueous acid such as dilute HCl.

We also provide an alternative process for preparing a compound of formula (II) which comprises:
(a) reacting a compound of formula (III) with an activated derivative of 2-furoic acid in an amount of at least 2 moles of activated derivative per mole of compound of formula (III) to yield a compound of formula (IIA); and
(b) removal of the sulphur-linked 2-furoyl moiety from compound of formula (IIA) by reaction of the product of step (a) with a further mole of compound of formula (III) to give two moles of compound of formula (II).

In step (a) preferably the activated derivative of 2-furoic acid may be an activated ester of 2-furoic acid, but is more preferably a 2-furoyl halide, especially 2-furoyl chloride. A suitable solvent for his step is acetone. Normally an organic base e.g. triethylamine will be present. In step (b) a suitable solvent is DMF or dimethylacetamide. Normally an organic base e.g. triethylamine will be present. Generally steps (a) and (b) will be performed at reduced temperature e.g. between 0 and 5° C. The product may be isolated by treatment with acid and washing with water.

This aforementioned process is very efficient in that it does not produce any furoylamide by-product (thus affording inter alia environmental advantages) since the excess mole of furoyl moiety is taken up by reaction with a further mole of compound of formula (II) to form an additional mole of compound of formula (II).

Further general conditions for the conversion of compound of formula (III) to compound of formula (II) in the two processes just described will be well known to persons skilled in the art.

According to a preferred set of conditions, however, we have found that the compound of formula (II) may advantageously be isolated in the form of a solid crystalline salt. The preferred salt is a salt formed with a base such as triethylamine, 2,4,6-trimethylpyridine, diisopropylethylamine or N-ethylpiperidine. Such salt forms of compound of formula (II) are more stable, more readily filtered and dried and can be isolated in higher purity than the free thioacid. The most preferred salt is the salt formed with diisopropylethylamine. The triethylamine salt is also of interest.

Compounds of formula (III) may be prepared in accordance with procedures described in GB 2088877B.

Compounds of formula (III) may also be prepared by a process comprising the following steps:

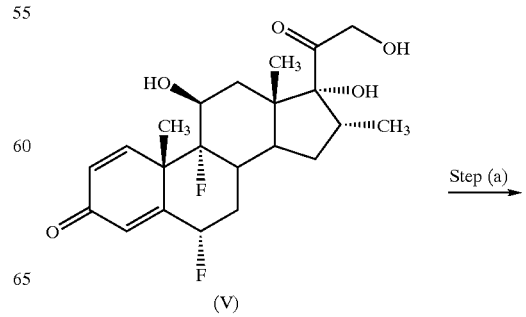

Step (a) →

(V)

-continued

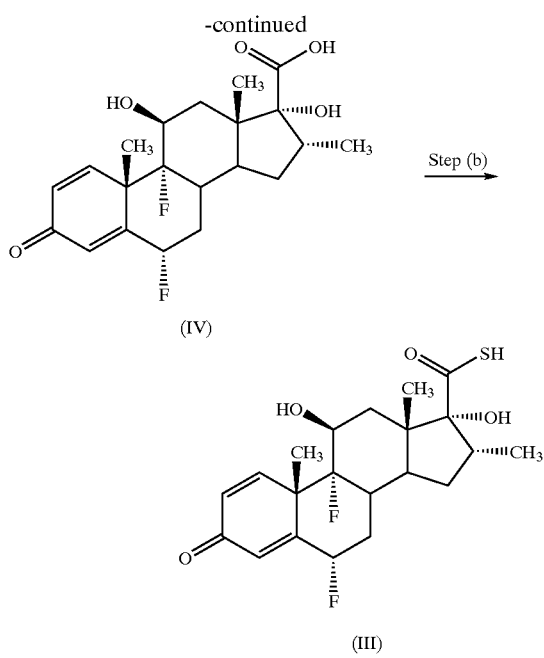

(IV)

(III)

Step (a) comprises oxidation of a solution containing the compound of formula (V). Preferably, step (a) will be performed in the presence of a solvent comprising methanol, water, tetrahydrofuran, dioxan or diethylene glygol dimethylether. So as to enhance yield and throughput, preferred solvents are methanol, water or tetrahydrofuran, and more preferably are water or tetrahydrofuran, especially water and tetrahydrofuran as solvent. Dioxan and diethylene glygol dimethylether are also preferred solvents which may optionally (and preferably) be employed together with water. Preferably, the solvent will be present in an amount of between 3 and 10 vol relative to the amount of the starting material (1 wt.), more preferably between 4 and 6 vol., especially 5 vol. Preferably the oxidising agent is present in an amount of 1–9 molar equivalents relative to the amount of the starting material. For example, when a 50% w/w aqueous solution of periodic acid is employed, the oxidising agent may be present in an amount of between 1.1 and 10 wt. relative to the amount of the starting material (1 wt.), more preferably between 1.1 and 3 wt., especially 1.3 wt. Preferably, the oxidation step will comprise the use of a chemical oxidising agent. More preferably, the oxidising agent will be periodic acid or iodic acid or a salt thereof. Most preferably, the oxidising agent will be periodic acid or sodium periodate, especially periodic acid. Alternatively (or in addition), it will also be appreciated that the oxidation step may comprise any suitable oxidation reaction, e.g. one which utilises air and/or oxygen. When the oxidation reaction utilises air and/or oxygen, the solvent used in said reaction will preferably be methanol. Preferably, step (a) will involve incubating the reagents at room temperature or a little warmer, say around 25° C. e.g. for 2 hours. The compound of formula (IV) may be isolated by recrystallisation from the reaction mixture by addition of an anti-solvent. A suitable anti-solvent for compound of formula (IV) is water. Surprisingly we have discovered that it is highly desirable to control the conditions under which the compound of formula (IV) is precipitated by addition of anti-solvent e.g. water. When the recrystallisation is performed using chilled water (e.g. water/ice mixture at a temperature of 0–5° C.) although better anti-solvent properties may be expected we have found that the crystalline product produced is very voluminous, resembles a soft gel and is very difficult to filter. Without being limited by theory we believe that this low density product contains a large amount of solvated solvent within the crystal lattice. By contrast when conditions of around 10° C. or higher are used (e.g. around ambient temperature) a granular product of a sand like consistency which is very easily filtered is produced. Under these conditions, crystallisation typically commences after around 1 hour and is typically completed within a few hours (e.g. 2 hours). Without being limited by theory we believe that this granular product contains little or no solvated solvent within the crystal lattice.

Step (b) will typically comprise the addition of a reagent suitable for converting a carboxylic acid to a carbothioic acid e.g. using hydrogen sulphide gas together with a suitable coupling agent e.g. carbonyidiimidazole (CDl) in the presence of a suitable solvent e.g. dimethylformamide.

The advantages of the composition comprising a compound of formula (I) together with a guest compound according to the invention may include the fact that the substance appears to demonstrate excellent anti-inflammatory properties, with predictable pharmacokinetic and pharmacodynamic behaviour, with an attractive side-effect profile, long duration of action, and is compatible with a convenient regime of treatment in human patients, in particular being amenable to once-per day dosing. Further advantages may include the fact that the substance has desirable physical and chemical properties which allow for ready manufacture and storage. Alternatively it may serve as a useful intermediate in the preparation of other forms of the compound of formula (I) or compositions thereof.

DETAILED DESCRIPTION

The following non-limiting Examples illustrate the invention:

EXAMPLES

General $^1$H-nmr spectra were recorded at 400 MHz and the chemical shifts are expressed in ppm relative to tetramethylsilane. The following abbreviations are used to describe the multiplicities of the signals: s (singlet), d (doublet), t (triplet), q (quartet), m (multiplet), dd (doublet of doublets), ddd (doublet of doublet of doublets), dt (doublet of triplets) and b (broad). Biotage refers to prepacked silica gel cartridges containing KP-Sil run on flash 12i chromatography module. LCMS was conducted on a Supelcosil LCABZ+ PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0–0.7 min 0% B, 0.7–4.2 min 100% B, 4.2–5.3 min 0% B, 5.3–5.5 min 0% B at a flow rate of 3 ml/min. The mass spectra were recorded on a Fisons VG Platform spectrometer using electrospray positive and negative mode (ES+ve and ES−ve).

Figure 1:
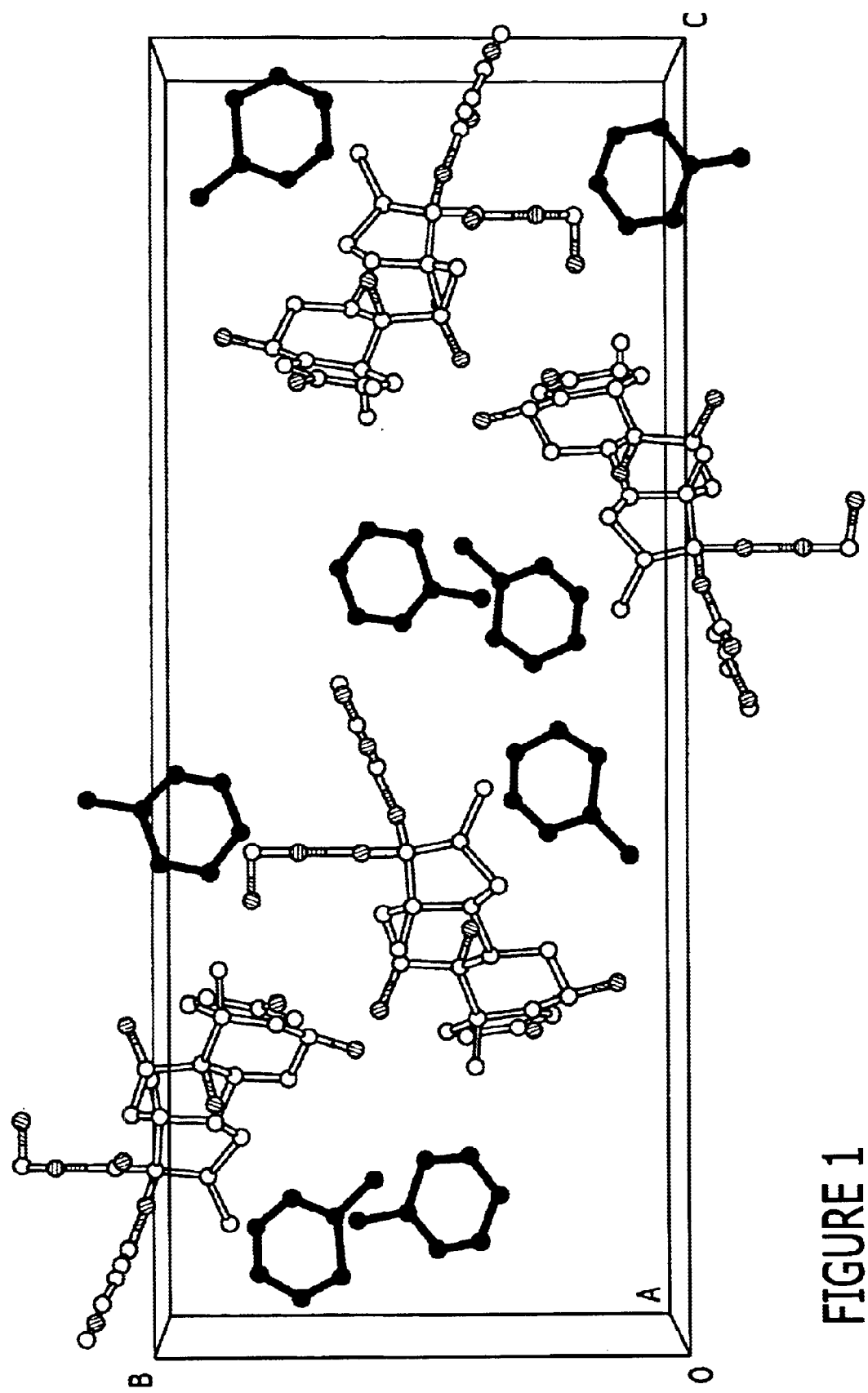
FIG. 1: Figure showing the spacial arrangement of 4 steroid and 8 guest molecules in the unit cell of a composition of the invention with toluene (guest molecule darkened).
Figure 2:
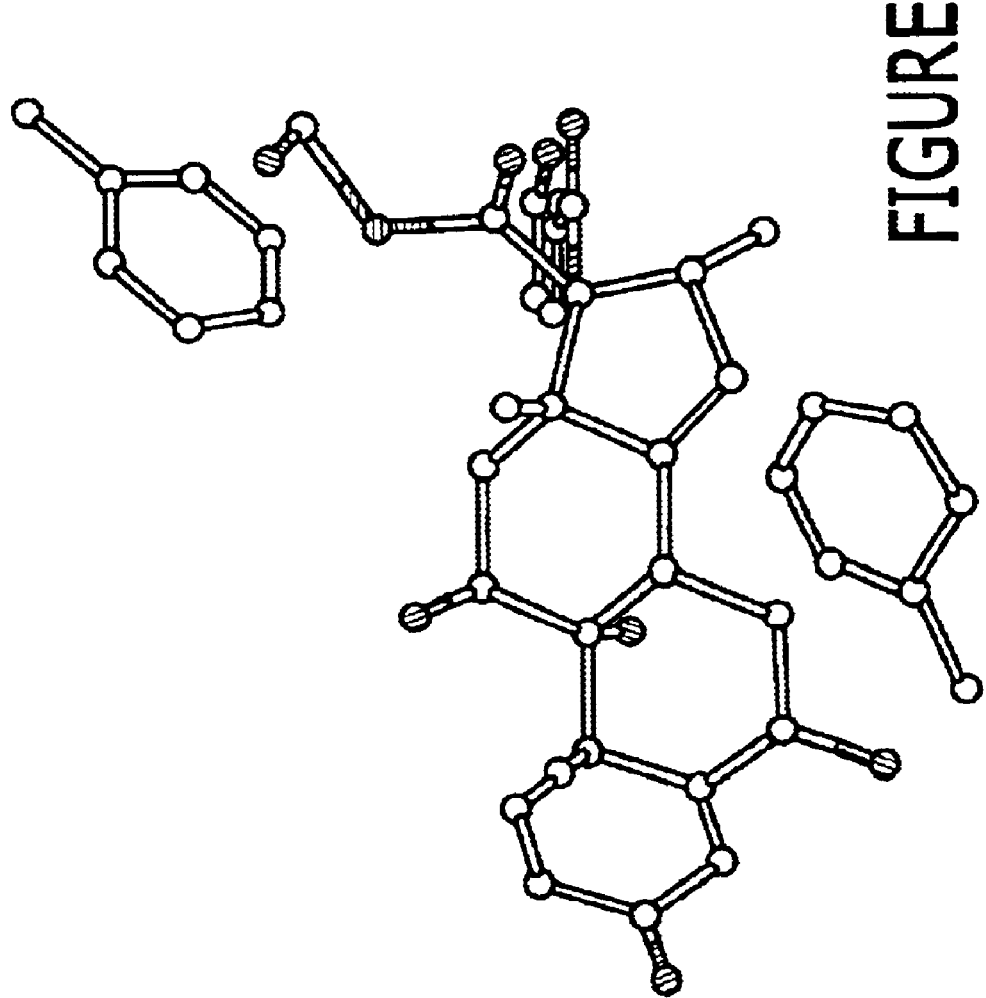
FIG. 2: Figure showing hydrogen bond interactions between steroid and guest for the composition of the invention with toluene
Figure 3:
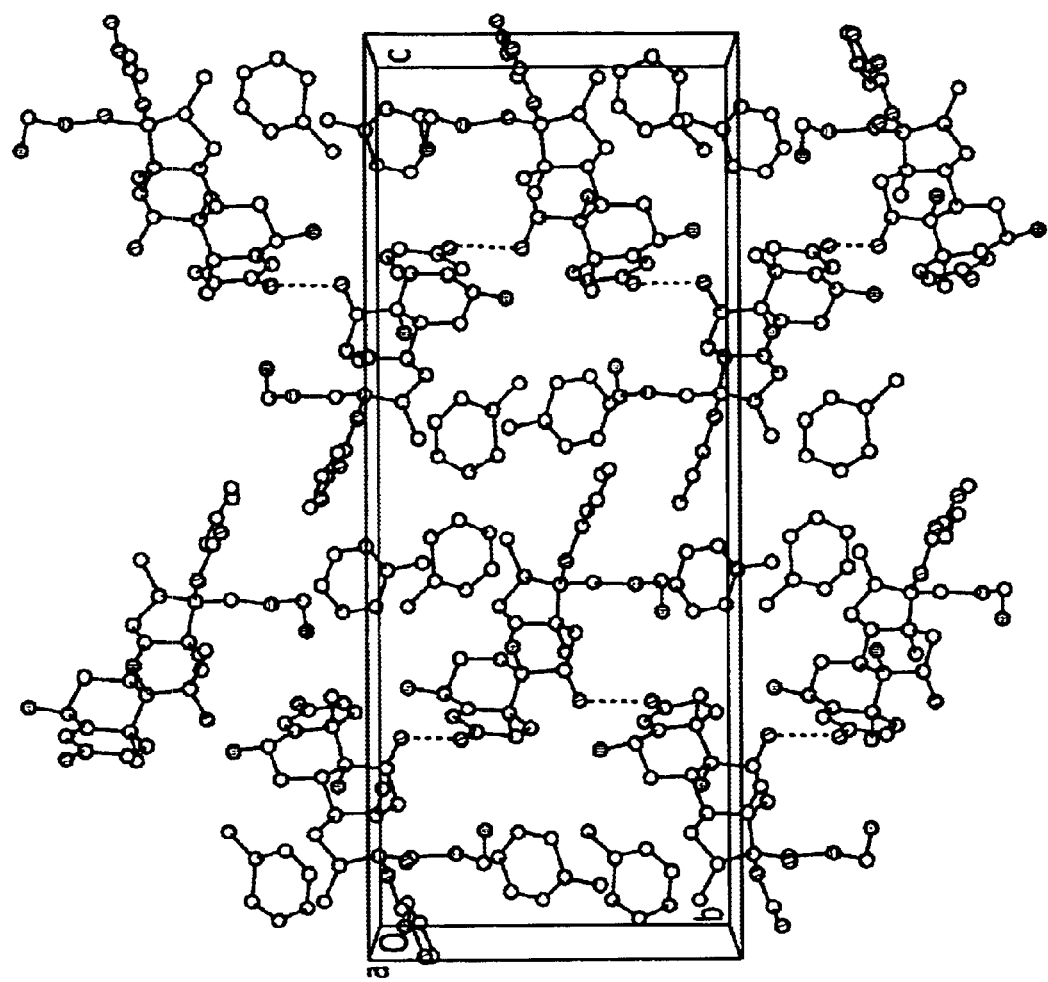
FIG. 3: Figure showing the spacial arrangement of 4 steroid and 8 guest molecules in the unit cell of a composition of the invention with toluene, and hydrogen bond interactions between two steroid molecules
Figure 4:
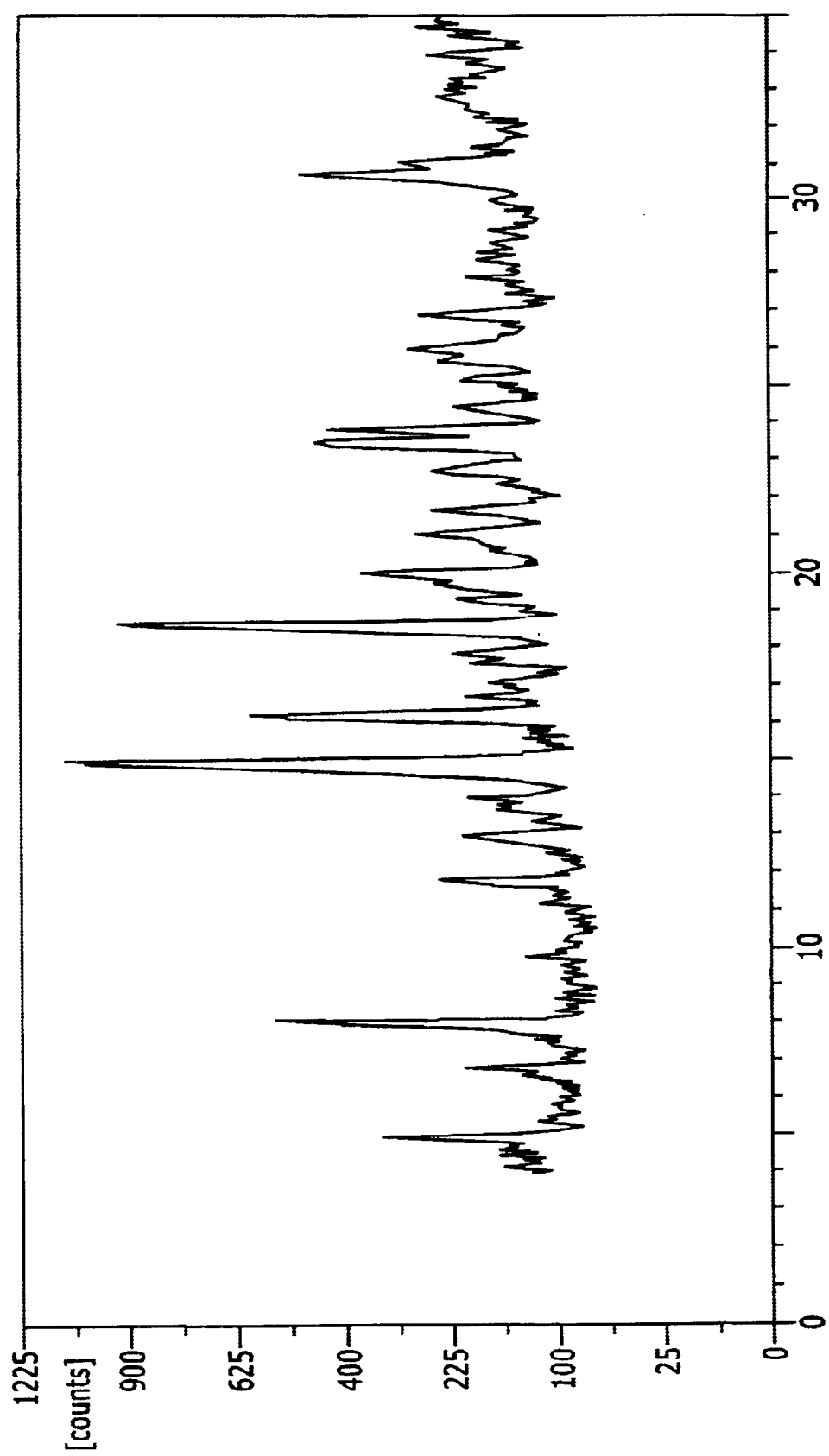
FIG. 4: Enlarged XRPD profile of composition of the invention with toluene
Figure 5:
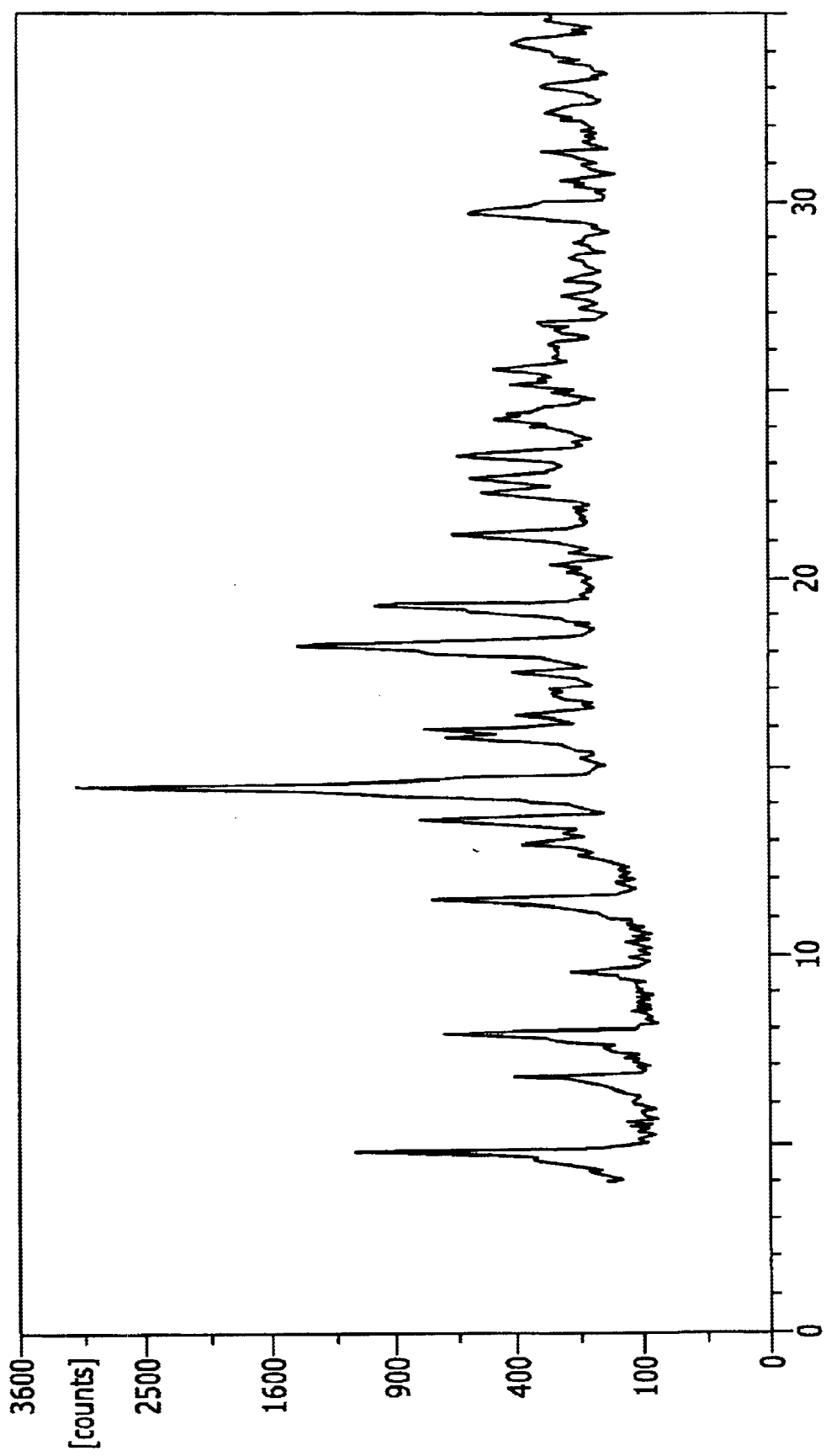
FIG. 5: Enlarged XRPD profile of composition of the invention with m-xylene
Figure 6:
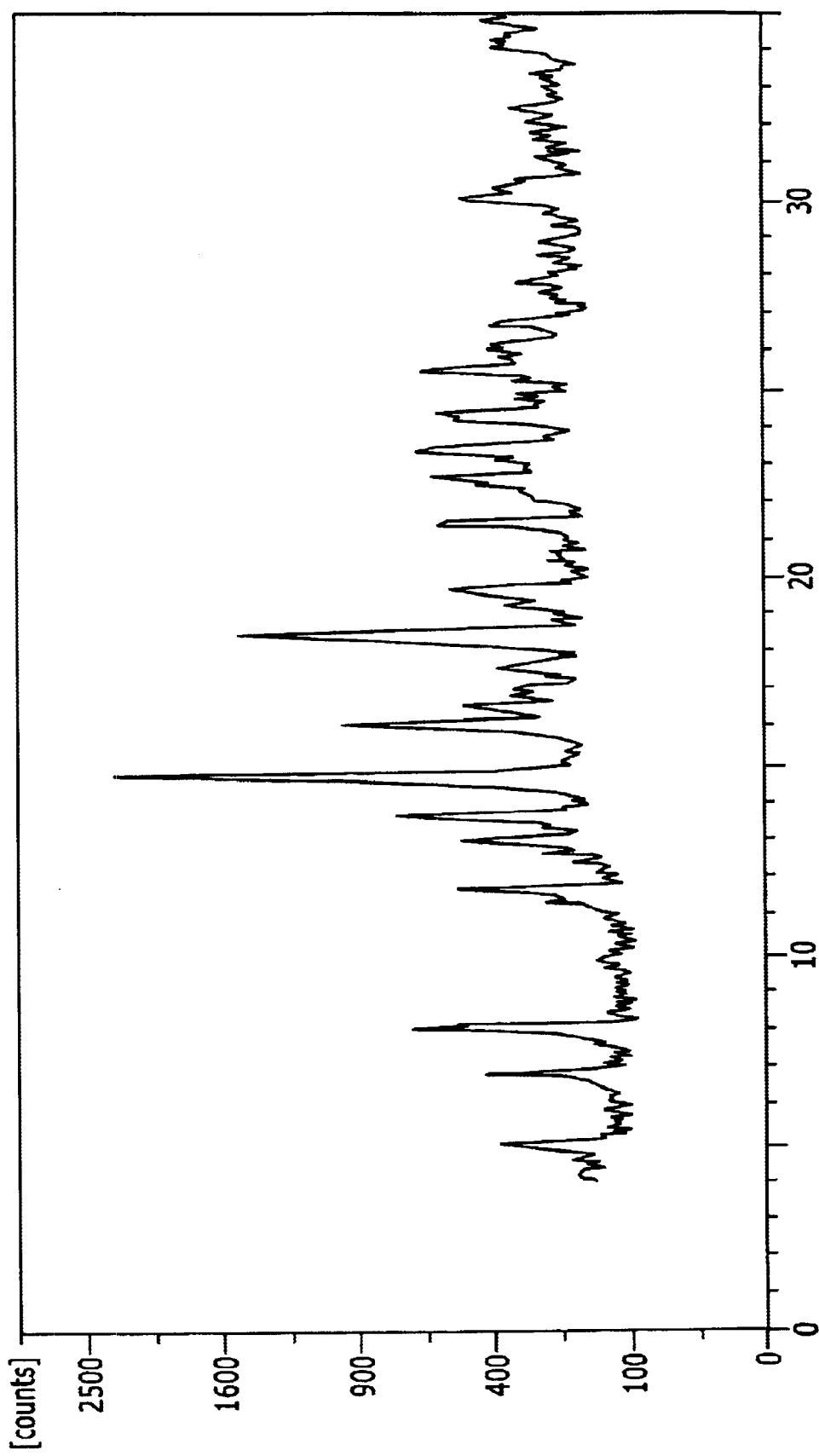
FIG. 6: Enlarged XRPD profile of composition of the invention with o-xylene
Figure 7:
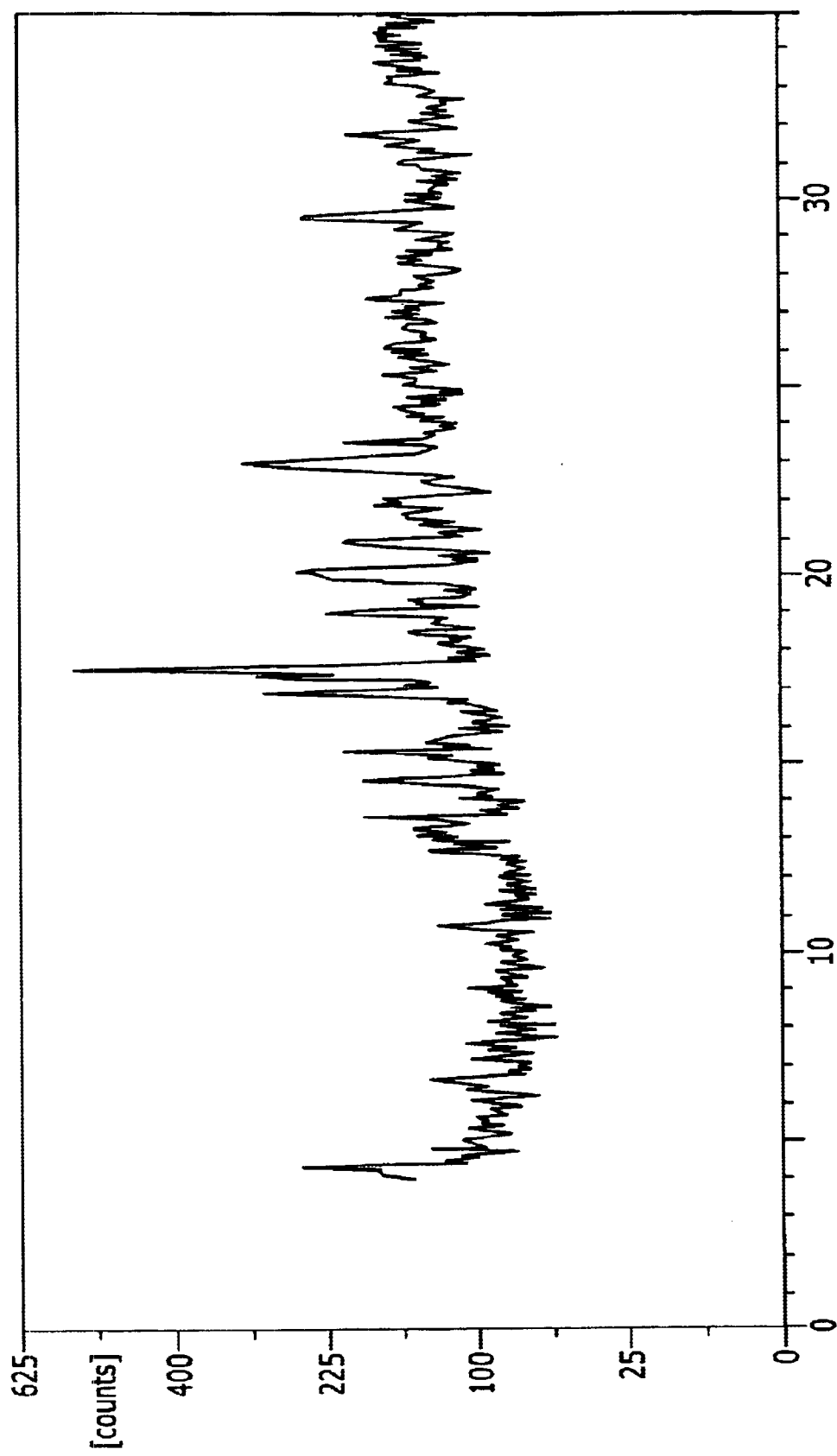
FIG. 7: Enlarged XRPD profile of composition of the invention with chlorobenzene
Figure 8:
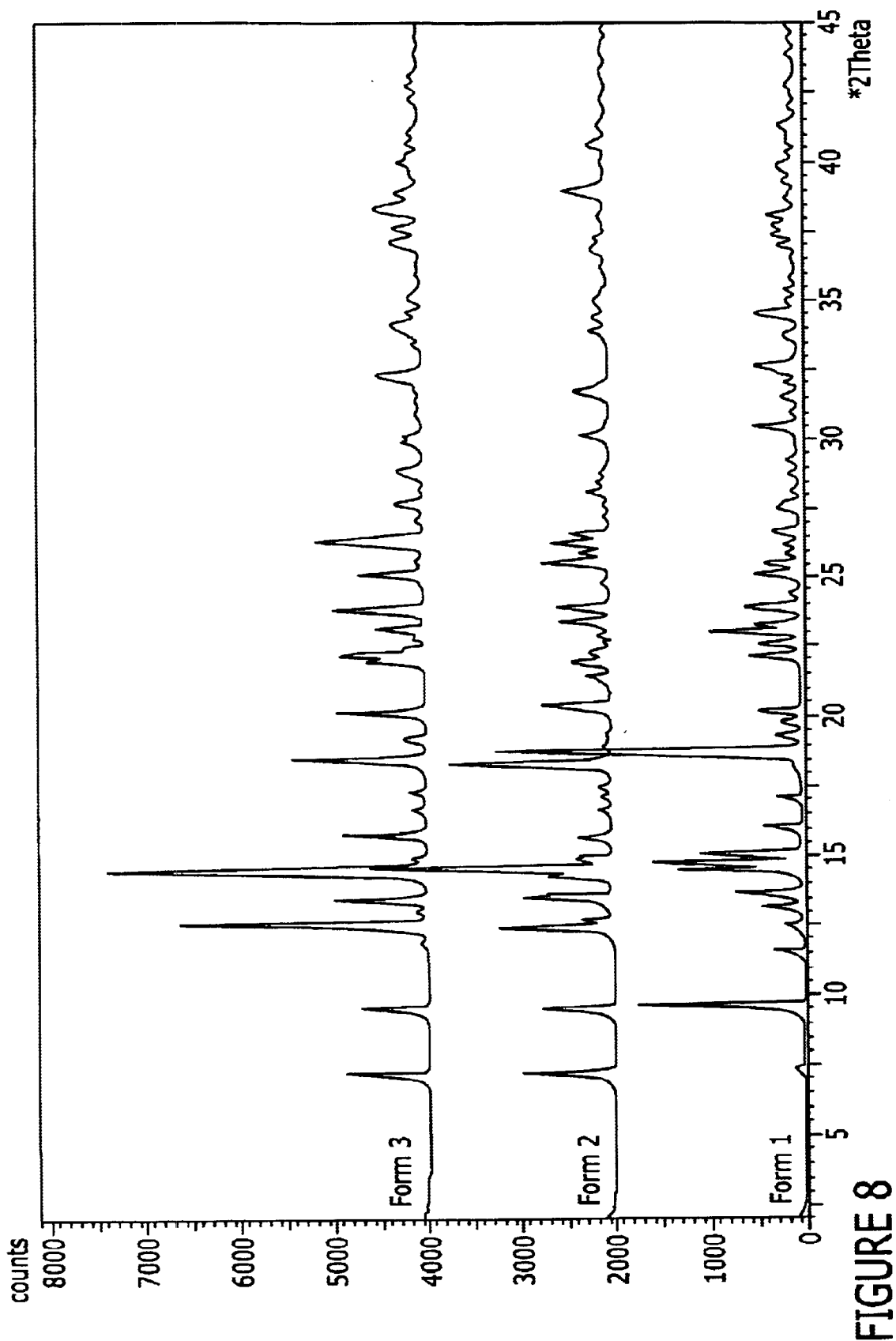
FIG. 8: XRPD profiles of unsolvated polymorphs 1, 2 and 3

The XRPD analyses shown in the figures were performed on a) a Phillips X'pert MPD powder diffractometer, serial number DY667. The pattern was recorded using the following acquisition conditions: Tube anode: Cu, Start angle: 2.0°2θ, End angle: 45.0°2θ, Step size: 0.02°2θ, Time per step: 1 second. XRPD profiles were collected at ambient temperature (295K) (FIG. 8);

b) a Philips PW1710 powder diffractometer. The pattern was recorded using the following acquisition conditions: Tube anode: Cu, Start angle: 3.5°2θ, End angle: 35.0°2θ, Step size: 0.02°2θ, Time per step: 2.3 seconds. XRPD profiles were collected at ambient temperature (295K) (FIGS. 4–7);

The diffractometer used in each case can be determined by the end angle in the figure.

X-ray diffraction pattern collections referred to in Table 1 were performed in the following manners:

The crystal and molecular structures and corresponding unit cell dimensions were determined from three-dimensional X-ray diffraction data collected at 120+/−2 K. All measurements were made using a Bruker SMART CCD diffractometer with graphite monochromated Mo-Kα radiation (λ=0.71073 Å) from a fine focus sealed tube source. The structure was solved by direct methods and refined using full-matrix least-squares procedures which minimized the function $Sw(Fo^2-Fc^2)^2$. The Bruker SHELX software was used throughout.

Intermediates

Intermediate 1: 6α,9α-Difluoro-17α-[(2-furanylcarbonyl)oxy]-11β-hydroxy-16α-methyl-3-oxo-androsta-1,4-diene-17β-carbothioic acid diisopropylethylamine salt A stirred suspension of 6α,9α-difluoro-11β,17α-dihydroxy-16α-methyl-3-oxo-androsta-1,4-diene-17β-carbothioic acid (prepared in accordance with the procedure described in GB 2088877B) (49.5 g) in methylacetate (500 ml) is treated with triethylamine (35 ml) maintaining a reaction temperature in the range 0–5° C. 2-Furoyl chloride (25 ml) is added and the mixture stirred at 0–5° C. for 1 hour. A solution of diethanolamine (52.8 g) in methanol (50 ml) is added and the mixture stirred at 0–5° C. for at least 2 hours. Dilute hydrochloric acid (approx 1 M, 550 ml) is added maintaining a reaction temperature below 15° C. and the mixture stirred at 15° C. The organic phase is separated and the aqueous phase is back extracted with methyl acetate (2×250 ml). All of the organic phases are combined, washed sequentially with brine (5×250 ml) and treated with di-isopropylethylamine (30 ml). The reaction mixture is concentrated by distillation at atmospheric pressure to an approximate volume of 250 ml and cooled to 25–30° C. (crystallisation of the desired product normally occurs during distillation/subsequent cooling). Tertiary butyl methyl ether (TBME) (500 ml) is added, the slurry further cooled and aged at 0–5° C. for at least 10 minutes. The product is filtered off, washed with chilled TBME (2×200 ml) and dried under vacuum at approximately 40–50° C. (75.3 g, 98.7%). NMR ($CDCl_3$) δ: 7.54–7.46 (1H, m), 7.20–7.12 (1H, dd), 7.07–6.99 (1H, dd), 6.48–6.41 (2H, m), 6.41–6.32 (1H, dd), 5.51–5.28 (1H, dddd $^2J_{H-F}$ 50 Hz), 4.45–4.33(1H, bd), 3.92–3.73 (3H, bm), 3.27–3.14 (2H, q), 2.64–2.12 (5H, m), 1.88–1.71 (2H, m), 1.58–1.15 (3H, s), 1.50–1.38 (15H, m), 1.32–1.23 (1H, m), 1.23–1.15 (3H s), 1.09–0.99 (3H, d)

Intermediate 2: 6α,9α-Difluoro-17α-[(2-furanylcarbonyl)oxy]-11β-hydroxy-16α-methyl-3-oxo-androsta-1,4-diene-17β-carbothioic acid S-fluoromethyl ester Unsolvated Form 1

A mobile suspension of Intermediate 1 (12.61 g, 19.8 mmol) in ethyl acetate (230 ml) and water (50 ml) is treated with a phase transfer catalyst (benzyltributylammonium chloride, 10 mol %), cooled to 3° C. and treated with bromofluoromethane (1.10 ml, 19.5 mmol, 0.98 equivalents), washing in with prechilled (0° C.) ethyl acetate (EtOAc) (20 ml). The suspension is stirred overnight, allowing to warm to 17° C. The aqueous layer is separated and the organic phase is sequentially washed with 1 M HCl (50 ml), 1% w/v $NaHCO_3$ solution (3×50 ml) and water (2×50 ml). The ethylacetate solution is distilled at atmospheric pressure until the distillate reaches a temperature of approximately 73° C. at which point toluene (150 ml) is added. Distillation is continued at atmospheric pressure until all remaining EtOAc has been removed (approximate distillate temperature 103° C.). The resultant suspension is cooled and aged at <10° C. and filtered off. The bed is washed with toluene (2×30 ml) and the product oven dried under vacuum at 60° C. to constant weight to yield the title compound (8.77 g, 82%) LCMS retention time 3.66 min, m/z 539 $MH^+$, NMR δ ($CDCl_3$) includes 7.60 (1H, m), 7.18–7.11 (2H, m), 6.52 (1H, dd, J 4.2 Hz), 6.46 (1H, s), 6.41 (1H, dd, J 10, 2 Hz), 5.95 and 5.82 (2H dd, J 51, 9 Hz), 5.48 and 5.35 (1H, 2m), 4.48 (1H, m), 3.48 (1H, m), 1.55 (3H, s), 1.16 (3H, s), 1.06 (3H, d, J 7 Hz).

Pharmacological Activity

In Vitro Pharmacological Activity

Pharmacological activity was assessed in a functional in vitro assay of glucocorticoid agonist activity which is generally predictive of anti-inflammatory or anti-allergic activity in vivo.

For the experiments in this section, compound of formula (I) was used as unsolvated Form 1 (Intermediate 2)

The functional assay was based on that described by K. P. Ray et al., Biochem J. (1997), 328, 707–715. A549 cells stably transfected with a reporter gene containing the NF-κB responsive elements from the ELAM gene promoter coupled to sPAP (secreted alkaline phosphatase) were treated with test compounds at appropriate doses for 1 hour at 37° C. The cells were then stimulated with tumour necrosis factor (TNF, 10 ng/ml) for 16 hours, at which time the amount of alkaline phosphatase produced is measured by a standard colourimetric assay. Dose response curves were constructed from which $EC_{50}$ values were estimated.

In this test the compound of formula (1) showed an $EC_{50}$ value of <1 nM.

The glucocorticoid receptor (GR) can function in at least two distinct mechanisms, by upregulating gene expression through the direct binding of GR to specific sequences in gene promotors, and by downregulating gene expression that is being driven by other transcription factors (such as NFκB or AP-1) through their direct interaction with GR.

In a variant of the above method, to monitor these functions, two reporter plasmids have been generated and introduced separately into A549 human lung epithelial cells by transfection. The first cell line contains the firefly luciferase reporter gene under the control of a synthetic promoter that specifically responds to activation of the transcription factor NFκB when stimulated with TNFα. The second cell line contains the renilla luciferase reporter gene under the control of a synthetic promotor that comprises 3 copies of the consensus glucocorticoid response element, and which responds to direct stimulation by glucocorticoids. Simultaneous measurement of transactivation and transrepression was conducted by mixing the two cell lines in a 1:1 ratio in 96 well plate (40,000 cells per well) and growing overnight at 37° C. Test compounds were dissolved in DMSO, and added to the cells at a final DMSO concentration of 0.7%. After incubation for 1 h 0.5 ng/ml TNFα (R&D Systems) was added and after a further 15 hours at 37° C., the levels of firefly and renilla luciferase were measured using the Packard Firelite kit following the manufacturers' directions. Dose response curves were constructed from which $EC_{50}$ values were determined.

|  | Transactivation (GR) $ED_{50}$ (nM) | Transrepression (NFκB) $ED_{50}$ (nM) |
|---|---|---|
| Compound of Formula (I) | 0.06 | 0.20 |
| Metabolite (X) | >250 | >1000 |
| Fluticasone propionate | 0.07 | 0.16 |

In Vivo Pharmacological Activity

Pharmacological activity in vivo was assessed in an ovalbumin sensitised Brown Norway rat eosinophilia model. This model is designed to mimic allergen induced lung eosinophilia, a major component of lung inflammation in asthma.

For the experiments in this section, compound of formula (I) was used as unsolvated Form 1.

Compound of formula (I) produced dose dependant inhibition of lung eosinophilia in this model after dosing as an intra-tracheal (IT) suspension in saline 30 min prior to ovalbumin challenge. Significant inhibition is achieved after a single dose of 30 μg of compound of formula (I) and the response was significantly (p=0.016) greater than that seen with an equivalent dose of fluticasone propionate in the same study (69% inhibition with compound of formula (I) vs 41% inhibition with fluticasone propionate).

In a rat model of thymus involution 3 daily IT doses of 100 μg of compound (I) induced significantly smaller reductions in thymus weight (p=0.004) than an equivalent dose of fluticasone propionate in the same study (67% reduction of thymus weight with compound (I) vs 78% reduction with fluticasone propionate).

Taken together these results indicate a superior therapeutic index for compound (I) compared to fluticasone propionate.

In Vitro Metabolism in Rat and Human Hepatocytes

Incubation of compound (I) with rat or human hepatocytes shows the compound to be metabolised in an identical manner to fluticasone propionate with the 17-β carboxylic acid (X) being the only significant metabolite produced. Investigation of the rate of appearance of this metabolite on incubation of compound (I) with human hepatocytes (37° C., 10 μM drug concentration, hepatocytes from 3 subjects, 0.2 and 0.7 million cells/mL) shows compound (I) to be metabolised ca. 5-fold more rapidly than fluticasone propionate:

| Subject number | Cell density (million cells/mL) | 17-β acid metabolite production (pmol/h) | |
|---|---|---|---|
|  |  | Compound (I) | Fluticasone propionate |
| 1 | 0.2 | 48.9 | 18.8 |
| 1 | 0.7 | 73.3 | 35.4 |
| 2 | 0.2 | 118 | 9.7 |
| 2 | 0.7 | 903 | 23.7 |
| 3 | 0.2 | 102 | 6.6 |
| 3 | 0.7 | 580 | 23.9 |

Median metabolite production 102–118 pmol/h for compound (I) and 18.8–23.0 pmol/h for fluticasone propionate.

Pharmacokinetics After Intravenous (IV) and Oral Dosing in Rats

Compound (I) was dosed orally (0.1 mg/kg) and IV (0.1 mg/kg) to male Wistar Han rats and pharmacokinetic parameters determined. Compound (I) showed negligible oral bioavailability (0.9%) and plasma clearance of 47.3 mL/min/kg, approaching liver blood flow (plasma clearance of fluticasone propionate=45.2 mL/min/kg).

Pharmacokinetics After Intra-tracheal Dry Powder Dosing in the Pig.

Anaesthetised pigs (2) were dosed intra-tracheally with a homogenous mixture of compound (I) (1 mg) and fluticasone propionate (1 mg) as a dry powder blend in lactose (10% w/w). Serial blood samples were taken for up to 8 h following dosing. Plasma levels of compound (I) and fluticasone propionate were determined following extraction and analysis using LC-MS/MS methodology, the lower limits of quantitation of the methods were 10 and 20 pg/mL for compound (I) and fluticasone propionate respectively. Using these methods compound (I) was quantifiable up to 2 hours after dosing and fluticasone propionate was quantifiable up to 8 hours after dosing. Maximum plasma concentrations were observed for both compounds within 15 min after dosing. Plasma half-life data obtained from IV dosing (0.1 mg/kg) was used to calculate AUC (0-inf) values for compound (I). This compensates for the plasma profile of Compound (I) only being defined up to 2 hours after an IT dose and removes any bias due to limited data between compound (I) and fluticasone propionate.

$C_{max}$ and AUC (0-inf) values show markedly reduced systemic exposure to compound (I) compared to fluticasone propionate:

|  | Cmax (pg/mL) | | AUC (0-inf) (hr. pg/mL) | |
|---|---|---|---|---|
|  | Pig 1 | Pig 2 | Pig 1 | Pig 2 |
| Compound of Formula (I) | 117 | 81 | 254 | 221 |
| Fluticasone propionate | 277 | 218 | 455 | 495 |

The pharmacokinetic parameters for both compound (I) and fluticasone propionate were the same in the anaesthetised pig following intravenous administration of a mixture of the two compounds at 0.1 mg/kg. The clearance of these two glucocorticoids is similar is this experimental pig model.

Intermediate 3: 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, amorphous particles Intermediate 2 (30.04 g) was dissolved in methylethylketone (850 ml) to give a 3.5% solution. The solution was spray dried using a Niro Mobile Minor spray drier (Niro Inc, Columbia, Md., USA). The spray orifice was a two fluid pneumatic nozzle with 0.04 inch orifice diameter (Spray Systems Co, Wheaton, Ill., USA). The other spray drying parameters were as follows:

Temperature: 150° C., outlet temperature 98° C.

Solution flow rate: 30 ml/min using Isco 260D syringe pump (Isco Inc, Lincoln, Nev., USA)

Atomisation Pressure: 2 Bar

Particle collection was achieved in the conventional manner using a Fisher Klosterman XQ120–1.375 high efficiency cyclone (Fisher-Klosterman Inc, Louisville, Ky., USA). A white powder was recovered. The spray drying process was successful at producing smooth, spherical particles of amorphous 6α,9α-Difluoro-17α-[(2-furanylcarbonyl)oxy]-11β-hydroxy-16α-methyl-3-oxo-androsta-1,4-diene-17β-carbothioic acid S-fluoromethyl ester. System yield was 61%

Intermediate 4 6α,9α-Difluoro-17α-[(2-furanylcarbonyl)oxy]-11β-hydroxy-16α-methyl-3-oxo-androsta-1,4-diene-17β-carbothioic acid S-fluoromethyl ester Unsolvated Form 2

EXAMPLES

Example 1

6α,9α-Difluoro-17α-[(2-furanylcarbonyl)oxy]-11β-hydroxy-16α-methyl-3-oxo-androsta-1,4-diene-17β-carbothioic acid S-fluoromethyl ester Composition with Toluene Intermediate 4 (200 mg) was slurried in toluene (5 mL) for 3 hours. The solid was then recovered by filtration to afford the title compound as a white solid.

Stoichiometry of compound of formula (I): guest=1: 3.1 from $^1$H nmr (CDCl$_3$).

Example 2

6α,9α-Difluoro-17α-[(2-furanylcarbonyl)oxy]-11β-hydroxy-16α-methyl-3-oxo-androsta-1,4-diene-17β-carbothioic acid S-fluoromethyl ester Composition with m-xylene Intermediate 4 (200 mg) was slurried in m-xylene (6 mL) for 2 hours. The solid was then recovered by filtration to afford the title compound as a white solid.

Example 3

6α,9α-Difluoro-17α-[(2-furanylcarbonyl)oxy]-11β-hydroxy-16α-methyl-3-oxo-androsta-1,4-diene-17β-carbothioic acid S-fluoromethyl ester Composition with o-xylene (first alternative method)

Intermediate 3 (100 mg) was slurried in o-xylene (1 mL) at 21° C. for 16 hours. The solid was recovered by filtration to afford the title compound as a white solid. Stoichiometry of compound of formula (I): guest=1: 1.5 from $^1$H nmr (CDCl$_3$).

Example 4

6α,9α-Difluoro-17α-[(2-furanylcarbonyl)oxy]-11β-hydroxy-16α-methyl-3-oxo-androsta-1,4-diene-17β-carbothioic acid S-fluoromethyl ester Composition with o-xylene (second alternative method)

Intermediate 2 (3.0 g) was dissolved in a mixture of o-xylene (60 mL) and acetonitrile (60 mL). The solvent was allowed to evaporate under ambient conditions until the crystallisation had proceeded sufficiently. The solid was then recovered by filtration to afford the title compound as a white solid.

Stoichiometry of compound of formula (I): guest=1: 4 from $^1$H nmr (CDCl$_3$).

Example 5

6α,9α-Difluoro-17α-[(2-furanylcarbonyl)oxy]-11β-hydroxy-16α-methyl-3-oxo-androsta-1,4-diene-17β-carbothioic acid S-fluoromethyl ester Composition with Chlorobenzene Intermediate 4 (200 mg) was slurried in m-xylene (5 mL) for 3 hours. The solid was then recovered by filtration to afford the title compound as a white solid.

Further characterising data on compositions of the invention:

Detailed XRPD profile peak information for various compositions of the invention is provided in Tables 2, 3, 4 and 5.

The XRPD profiles of compositions of the invention are provided in FIGS. 4, 5, 6 and 7.

We also claim compositions of the invention substantially by reference to their XRPD profiles as shown in the Figures and Tables.

Example A

Dry Powder Composition Containing 6α,9α-Difluoro-17α-[(2-furanylcarbonyl)oxy]-11β-hydroxy-16α-methyl-3-oxo-androsta-1,4-diene-17β-carbothioic acid S-fluoromethyl ester composition with toluene A dry powder formulation may be prepared as follows:

| | |
|---|---|
| 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, composition with toluene prepared according to Example 1, MMD of 3 μm: | 0.20 mg |
| milled lactose (wherein not greater than 85% of particles have a MMD of 60–90 μm, and not less than 15% of particles have a MMD of less than 15 μm): | 12 mg |
| A peelable blister strip containing 60 blisters each filled with a formulation as just described may be prepared. | |

Example B

Dry Powder Composition Containing 6α,9α-Difluoro-17α-[(2-furanylcarbonyl)oxy]-11β-hydroxy-16α-methyl-3-oxo-androsta-1,4-diene-17β-carbothioic acid S-fluoromethyl ester composition with toluene and a long acting β₂-adrenoreceptor agonist A dry powder formulation may be prepared as follows:

| | |
|---|---|
| 6α,9α-Difluoro-17α-[(2-furanylcarbonyl)oxy]-11β-hydroxy-16α-methyl-3-oxo-androsta-1,4-diene-17β-carbothioic acid S-fluoromethyl ester composition with toluene prepared according to Example 1, MMD of 3 μm: | 0.20 mg |
| Long-acting β₂-adrenoreceptor agonist (micronised to a MMD of 3 μm): | 0.20 mg |
| milled lactose (wherein not greater than 85% of particles have a MMD of 60–90 μm, and not less than 15% of particles have a MMD of less than 15 μm): | 12 mg |
| A peelable blister strip containing 60 blisters each filled with a formulation as just described may be prepared. | |

Example C

Aerosol Formulation Containing 6α,9α-Difluoro-17α-[(2-furanylcarbonyl)oxy]-11β-hydroxy-16α-methyl-3-oxo-androsta-1,4-diene-17β-carbothioic acid S-fluoromethyl ester composition with toluene prepared according to Example 1, MMD of 3 μm:

An aluminium canister may be filled with a fromulation as follows:

| | |
|---|---|
| 6α,9α-Difluoro-17α-[(2-furanylcarbonyl)oxy]-11β-hydroxy-16α-methyl-3-oxo-androsta-1,4-diene-17β-carbothioic acid S-fluoromethyl ester composition with toluene prepared according to Example 1, MMD of 3 μm: | 250 μg |
| 1,1,1,2-tetrafluoroethane: | to 50 μl |
| (amounts per actuation) in a total amount suitable for 120 actuations and the canister may be fitted with a metering valve adapted to dispense 50 μl per actuation. | |

Example D

Aerosol formulation containing 6α,9α-Difluoro-17α-[(2-furanylcarbonyl)oxy]-11β-hydroxy-16α-methyl-3-oxo-androsta-1,4-diene-17β-carbothioic acid S-fluoromethyl ester composition with toluene and a long acting β₂-adrenoreceptor agonist An aluminium canister may be filled with a formulation as follows:

| | |
|---|---|
| 6α,9α-Difluoro-17α-[(2-furanylcarbonyl)oxy]-11β-hydroxy-16α-methyl-3-oxo-androsta-1,4-diene-17β-carbothioic acid S-fluoromethyl ester composition with toluene prepared according to Example 1, MMD of 3 μm: | 250 μg |
| Long-acting β₂-adrenoreceptor agonist (micronised to a MMD of 3 μm): | 25 μg |
| 1,1,1,2-tetrafluoroethane: | to 50 μl |
| (amounts per actuation) in a total amount suitable for 120 actuations and the canister may be fitted with a metering valve adapted to dispense 50 μl per actuation. | |

Example E

Nasal formulation containing 6α,9α-Difluoro-17α-[(2-furanylcarbonyl)oxy]-11β-hydroxy-16α-methyl-3-oxo-androsta-1,4-diene-17β-carbothioic acid S-fluoromethyl ester composition with toluene A formulation for intranasal delivery may be prepared as follows:

| | |
|---|---|
| 6α,9α-Difluoro-17α-[(2-furanylcarbonyl)oxy]-11β-hydroxy-16α-methyl-3-oxo-androsta-1,4-diene-17β-carbothioic acid S-fluoromethyl ester composition with toluene prepared according to Example 1, MMD of 3 μm: | 10 mg |
| Polysorbate 20 | 0.8 mg |
| Sorbitan monolaurate | 0.09 mg |
| Sodium dihydrogen phosphate dihydrate | 94 mg |
| Dibasic sodium phosphate anhydrous | 17.5 mg |
| Sodium chloride | 48 mg |
| Demineralised water | to 10 ml |
| The formulation may be fitted into a spraypump capable of delivering a plurality of metered doses (Valois). | |

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The patents and patent applications described in this application are herein incorporated by reference.

TABLE 2

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, composition with toluene

| Angle 2-Theta ° | Rel. Intensity % |
|---|---|
| 4.9 | 25.6 |
| 6.8 | 12.2 |
| 8.0 | 43.6 |
| 9.9 | 1.7 |
| 11.8 | 15.5 |
| 13.0 | 13.1 |
| 14.0 | 12.9 |
| 15.0 | 100.0 |
| 16.3 | 53.2 |
| 16.7 | 12.0 |
| 17.9 | 14.2 |
| 18.7 | 83.2 |
| 19.4 | 13.3 |
| 20.1 | 26.6 |
| 21.1 | 19.7 |
| 21.7 | 17.2 |
| 22.8 | 14.5 |
| 23.5 | 37.2 |

TABLE 2-continued

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, composition with toluene

| Angle 2-Theta ° | Rel. Intensity % |
|---|---|
| 23.9 | 34.6 |
| 24.5 | 14.0 |
| 25.3 | 10.5 |
| 25.8 | 15.5 |
| 26.1 | 20.5 |
| 27.0 | 18.8 |
| 28.8 | 8.2 |
| 30.7 | 39.2 |
| 31.1 | 21.4 |
| 32.7 | 14.0 |
| 34.0 | 14.0 |
| 34.7 | 18.6 |

TABLE 3

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, composition with m-xylene

| Angle 2-Theta ° | Rel. Intensity % |
|---|---|
| 4.8 | 38.7 |
| 6.8 | 12.7 |
| 7.9 | 22.8 |
| 9.6 | 6.2 |
| 11.5 | 24.1 |
| 13.0 | 11.8 |
| 13.7 | 26.9 |
| 14.5 | 100.0 |
| 15.8 | 17.9 |
| 16.1 | 25.7 |
| 16.4 | 12.4 |
| 17.0 | 7.7 |
| 17.6 | 12.5 |
| 18.3 | 52.1 |
| 19.3 | 34.9 |
| 20.4 | 6.4 |
| 21.2 | 22.2 |
| 22.3 | 16.3 |
| 22.7 | 18.4 |
| 23.3 | 21.1 |
| 24.3 | 14.0 |
| 25.1 | 12.8 |
| 25.6 | 14.6 |
| 26.3 | 8.1 |
| 26.8 | 9.5 |
| 27.6 | 6.9 |
| 28.0 | 5.0 |
| 28.6 | 5.8 |
| 29.8 | 18.8 |
| 31.4 | 8.8 |
| 32.5 | 8.0 |
| 33.1 | 8.7 |
| 34.3 | 11.7 |

TABLE 4

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, composition with o-xylene

| Angle 2-Theta ° | Rel. Intensity % |
|---|---|
| 5.0 | 11.4 |
| 6.9 | 13.6 |
| 8.1 | 21.7 |
| 9.9 | 1.6 |
| 11.7 | 18.0 |
| 13.1 | 15.4 |
| 13.8 | 27.2 |
| 14.8 | 100.0 |
| 16.2 | 39.3 |
| 16.6 | 16.8 |
| 17.1 | 9.4 |
| 17.7 | 12.0 |
| 18.5 | 60.6 |
| 19.3 | 10.7 |
| 19.7 | 18.5 |
| 20.6 | 5.1 |
| 21.5 | 20.0 |
| 22.8 | 21.3 |
| 23.4 | 22.5 |
| 24.4 | 17.6 |
| 24.9 | 7.4 |
| 25.6 | 21.5 |
| 26.3 | 12.4 |
| 26.8 | 12.0 |
| 28.0 | 8.8 |
| 28.7 | 7.0 |
| 29.0 | 6.6 |
| 30.2 | 16.6 |
| 32.2 | 8.1 |
| 32.5 | 9.4 |
| 33.4 | 6.6 |
| 34.2 | 12.3 |

TABLE 5

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, composition with chlorobenzene

| Angle 2-Theta ° | Rel. Intensity % |
|---|---|
| 4.3 | 34.4 |
| 6.6 | 12.4 |
| 10.7 | 10.2 |
| 12.7 | 11.1 |
| 13.3 | 10.5 |
| 13.6 | 23.4 |
| 14.6 | 22.9 |
| 15.3 | 24.8 |
| 16.9 | 43.2 |
| 17.3 | 44.4 |
| 17.6 | 100.0 |
| 19.1 | 26.7 |
| 19.4 | 12.4 |
| 20.1 | 32.3 |
| 20.9 | 24.3 |
| 22.1 | 15.2 |
| 23.0 | 47.0 |
| 23.6 | 20.7 |
| 24.5 | 10.5 |
| 25.2 | 9.6 |
| 27.4 | 12.7 |
| 28.5 | 6.2 |
| 29.6 | 28.1 |

TABLE 5-continued

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, composition with chlorobenzene

| Angle 2-Theta ° | Rel. Intensity % |
|---|---|
| 31.8 | 17.5 |
| 33.3 | 6.2 |

What is claimed is:

1. A crystalline chemical composition comprising a compound of formula (I)

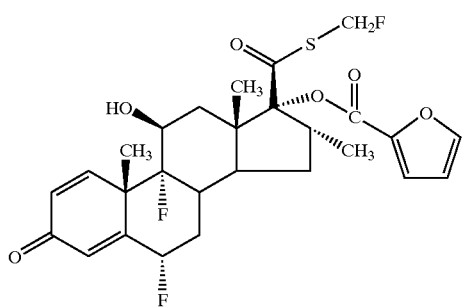

in which the crystal lattice is stabilised by the presence of a guest molecule, characterised in the crystalline composition is of space group $P2_12_12_1$ having unit cell dimensions of about 7.7±0.6 Å, 13.7±0.7 Å, and 37±3 Å when determined at 120K.

2. A composition according to claim 1 wherein the unit cell dimensions are 7.7±0.4 Å, 13.8±0.3 Å, and 36.8±3 Å when determined at 120K.

3. A composition according to claim 1 wherein the crystal lattice is stabilised by a hydrogen bonding interaction between the hydrogen atom of the C11 hydroxy on the compound of formula (I) with the oxygen of the C3 carbonyl on a second molecule of the compound of formula (I).

4. A composition according to claim 1 wherein the guest molecule has a relative molecular weight in the range 16 to 150.

5. A composition according to claim 1 wherein the guest molecule is toluene.

6. A composition according to claim 1 wherein the guest molecule is m-xylene.

7. A composition according to claim 1 wherein the guest molecule is o-xylene.

8. A composition according to claim 1 wherein the guest molecule is fluorobenzene.

9. A composition according to claim 1 wherein the guest molecule is chlorobenzene.

10. A composition according to claim 1 wherein the guest molecule is ethylbenzene.

11. A composition according to claim 1 wherein the ratio of compound of formula (I) to guest molecule is 1:5–0.25.

12. A pharmaceutical composition comprising a composition according to claim 1 together with a physiologically acceptable diluent or carrier.

13. A method for the treatment of a human or animal subject with an inflammatory and/or allergic condition, which method comprises administering to said human or animal subject an effective amount of the composition according to claim 1.

14. A pharmaceutical composition comprising a composition according to claim 1 in combination with another therapeutically active agent.

15. A composition according to claim 14 wherein the other therapeutically active ingredient is a long acting $\beta_2$-adrenoreceptor agonist.

16. A process for preparing a composition according to claim 1 which comprises (a) crystallising the composition from a solution containing a compound of formula (I) and the guest molecule; or (b) contacting the compound of formula (I) or another composition according claim 1 in solid form with a liquid containing the guest molecule and obtaining the composition therefrom; or (c) contacting a compound of formula (I) or another composition according to claim 1 in solid form with a vapour containing the guest molecule.

* * * * *